US012752065B2

(12) United States Patent
Hebrank et al.

(10) Patent No.: US 12,752,065 B2
(45) Date of Patent: Oct. 6, 2026

(54) DROPLET DELIVERY METHOD WITH MICRO-STOPPING DOSE METERING CAPABILITIES

(71) Applicant: PNEUMA RESPIRATORY, INC., Boone, NC (US)

(72) Inventors: John H. Hebrank, Boone, NC (US); Charles Eric Hunter, Boone, NC (US)

(73) Assignee: PNEUMA RESPIRATORY, INC., Boone, NC (US)

( * ) Notice: Subject to any disclaimer, the term of this patent is extended or adjusted under 35 U.S.C. 154(b) by 0 days.

(21) Appl. No.: 18/983,133

(22) Filed: Dec. 16, 2024

(65) Prior Publication Data

US 2025/0114542 A1 Apr. 10, 2025

Related U.S. Application Data

(63) Continuation of application No. 17/425,029, filed as application No. PCT/US2020/014785 on Jan. 23, 2020, now abandoned.

(Continued)

(51) Int. Cl.
*A61M 15/00* (2006.01)
*G16H 15/00* (2018.01)
*G16H 20/13* (2018.01)

(52) U.S. Cl.
CPC .... *A61M 15/0068* (2014.02); *A61M 15/0003* (2014.02); *A61M 15/0021* (2014.02);

(Continued)

(58) Field of Classification Search
CPC .......... A61M 15/0068; A61M 15/0003; A61M 15/0021; A61M 15/0066; A61M 2205/52;

(Continued)

(56) References Cited

U.S. PATENT DOCUMENTS 6,196,218 B1 * 3/2001 Voges .................... A24F 40/48
128/200.14
2002/0189615 A1 * 12/2002 Henry ............... A61M 15/0081
128/203.21

(Continued)

FOREIGN PATENT DOCUMENTS

JP 2003159332 A 6/2003
JP 2004148117 A 5/2004
JP 2005199066 A 7/2005

OTHER PUBLICATIONS

Japanese Office Action issued Oct. 3, 2023 in corresponding Japanese Application No. 2021-542364.

(Continued)

*Primary Examiner* — Timothy A Stanis
*Assistant Examiner* — Gwynneth L Howell
(74) *Attorney, Agent, or Firm* — Polsinelli PC

(57) ABSTRACT

Methods, devices and systems are provided wherein compositions are delivered to the pulmonary system of an intended user via inhalation in a controlled manner and at a desired doses and/or amounts, e.g., within a desired dosage window and/or inhalation topography. In certain embodiments, dosage windows and/or inhalation topography may be used, e.g., to provide for controlled cessation of use or to provide a desired therapeutic window.

15 Claims, 14 Drawing Sheets

Related U.S. Application Data

(60) Provisional application No. 62/906,652, filed on Sep. 26, 2019, provisional application No. 62/860,086, filed on Jun. 11, 2019, provisional application No. 62/823,335, filed on Mar. 25, 2019, provisional application No. 62/803,196, filed on Feb. 8, 2019, provisional application No. 62/796,561, filed on Jan. 24, 2019.

(52) U.S. Cl.
CPC ........ *A61M 15/0066* (2014.02); *G16H 15/00* (2018.01); *G16H 20/13* (2018.01); *A61M 2202/0007* (2013.01); *A61M 2202/04* (2013.01); *A61M 2205/3592* (2013.01); *A61M 2205/505* (2013.01); *A61M 2205/52* (2013.01)

(58) Field of Classification Search
CPC .............. A61M 15/00; A61M 15/0001; A61M 15/0065; A61M 15/007–0083; A61M 15/0091; A61M 15/0095; A61M 15/06; A24F 40/50; A24F 40/60
See application file for complete search history.

(56) References Cited

U.S. PATENT DOCUMENTS

| | | | | |
|---|---|---|---|---|
| 2005/0150489 | A1* | 7/2005 | Dunfield | A61M 15/0083 128/200.14 |
| 2005/0274377 | A1* | 12/2005 | Gonda | A61M 15/0051 128/200.14 |
| 2014/0174459 | A1* | 6/2014 | Burstyn | A24F 40/60 131/273 |
| 2016/0278435 | A1* | 9/2016 | Choukroun | A24F 40/65 |
| 2017/0146005 | A1* | 5/2017 | Edelen | A24F 40/50 |
| 2019/0014824 | A1 | 1/2019 | Yazbeck et al. | |
| 2020/0046918 | A1* | 2/2020 | Selby | A24F 40/40 |

OTHER PUBLICATIONS

Japanese Application No. 2021-542364, Decision to Grant a Patent mailed Apr. 25, 2024, 5 pages.

* cited by examiner

DROPLET DELIVERY METHOD WITH MICRO-STOPPING DOSE METERING CAPABILITIES

CROSS-REFERENCE TO RELATED APPLICATIONS

This application is a continuation of U.S. patent application Ser. No. 17/425,029, filed Jul. 22, 2021, which is a U.S. National Stage Application under 35 U.S.C. 371 of PCT Application No. PCT/US2020/014785, filed Jan. 23, 2020 entitled "ELECTRONIC BREATH ACTUATED DROPLET DELIVERY SYSTEMS WITH DOSE METERING CAPABILITIES, INHALATION TOPOGRAPHY METHODS, AND RELATED METHODS OF USE," which claims priority under 35 U.S.C. § 119(e) to U.S. Patent Application No. 62/796,561, filed Jan. 24, 2019 entitled "ELECTRONIC BREATH ACTUATED DROPLET DELIVERY DEVICE WITH DOSE METERING CAPABILITIES AND METHODS OF USE," U.S. Patent Application No. 62/803,196, filed Feb. 8, 2019, 2019 entitled "ELECTRONIC BREATH ACTUATED DROPLET DELIVERY DEVICE WITH DOSE METERING CAPABILITIES AND METHODS OF USE," U.S. Patent Application No. 62/823,335, filed Mar. 25, 2019 entitled "ELECTRONIC BREATH ACTUATED DROPLET DELIVERY DEVICE WITH DOSE METERING CAPABILITIES AND METHODS OF USE," U.S. Patent Application No. 62/860,086, filed Jun. 11, 2019 entitled "ELECTRONIC BREATH ACTUATED DROPLET DELIVERY DEVICE WITH DOSE METERING CAPABILITIES, INHALATION TOPOGRAPHY METHODS AND RELATED METHODS OF USE," and U.S. Patent Application No. 62/906,652, filed Sep. 26, 2019 entitled "ELECTRONIC BREATH ACTUATED DROPLET DELIVERY DEVICE WITH DOSE METERING CAPABILITIES, INHALATION TOPOGRAPHY METHODS AND RELATED METHODS OF USE," the entire contents of which are incorporated herein by reference in their entireties for all purposes.

FIELD OF THE INVENTION

This disclosure relates to droplet delivery systems and related methods and more specifically to droplet delivery systems and with dose metering capabilities and related methods for the delivery of fluids to the pulmonary system.

BACKGROUND OF THE INVENTION

The use of aerosol generating devices for the delivery of substances to the pulmonary system is an area of large interest. A major challenge is providing a device that delivers an accurate, consistent, and verifiable dose, with a droplet size that is suitable for successful delivery of substances to the targeted areas of the pulmonary system.

Dose verification, delivery and inhalation of the correct amount at desired times are also important. Problems emerge when users misuse or incorrectly administer material from inhalers and delivery devices.

Accordingly, there is a need for inhalation devices that deliver droplets of a suitable size range, with a dose that is controllable and verifiable, and provides feedback regarding correct and consistent usage of the device.

SUMMARY OF THE INVENTION

In one aspect of the disclosure, a method for controlling the dose and/or amount of a composition for delivery to the pulmonary system of a user via inhalation is provided. The method generally comprises receiving, at a computing system based on user input, a request for a desired dose or amount of at least one agent or ingredient of a composition for delivery to the pulmonary system of a user via inhalation; at the computing system and in response to receiving the request, determining inhalation delivery device operating parameters to provide the requested desired dose or amount of at least one agent or ingredient of a composition for delivery to the pulmonary system of a user via inhalation; generating, at the computing system, instructions for activation and operation of an inhalation delivery device to provide the requested desired dose or amount based on the determined inhalation delivery device operating parameters; and transmitting the instructions from the computing system to an ejector mechanism of an inhalation delivery device for execution at the inhalation delivery device to provide for activation and operation of the inhalation delivery device upon use to thereby control the dose and/or amount of the at least one agent or ingredient of a composition for delivery to the pulmonary system of user via inhalation.

In certain embodiments, the request for a desired dose or amount comprises an inhalation topography to achieve a desired dosing regimen. The inhalation topography may facilitate cessation of use. In some embodiments, the inhalation topography may gradually reduce the dose or amount over time to thereby facilitate cessation of use. In other embodiments, the inhalation topography may include an initial bolus dose at an initial loading dose, followed by maintenance doses at reduced dose.

In certain embodiments, the request includes independently selected doses and/or amounts at least two agents or ingredients such that instructions are provided to the inhalation delivery device to independently control the dose and/or amount of each of said at least two agents or ingredients separately.

In other embodiments, the composition may comprise nicotine, and the method may comprise controlling the dose or amount of nicotine for delivery to the pulmonary system of a user via inhalation. In certain embodiments, the composition may further comprise a flavoring, and the request may include independently selected doses and/or amounts for nicotine and the flavoring such that instructions are provided to the inhalation delivery device to independently control the dose and/or amount of each of nicotine and the flavoring separately.

In some embodiments, the computing system may be a user computing device, and the user input is received via a user interface of the user computing device. In other embodiments, an inhalation delivery device comprises the computing system, and the user input is received via a user interface of the inhalation delivery device, via input from user inhalation flowrates, or a combination thereof. The user interface of the inhalation delivery device may comprise user input buttons, an LCD touchscreen, or combinations thereof.

In other aspects, a computing system is provided. The computer system comprises one or more processors; and a memory storing instructions executable by the one or more processors, wherein, when executed by the one or more processors, the instructions cause the one or more processors to perform the method for controlling the dose and/or amount of a composition for delivery to the pulmonary system of a user via inhalation.

In certain embodiments, the method comprises receiving, based on user input, a request for a desired dose or amount of at least one agent or ingredient of a composition for delivery to the pulmonary system of a user via inhalation; determining inhalation delivery device operating parameters to provide the requested desired dose or amount of at least one agent or ingredient of a composition for delivery to the pulmonary system of a user via inhalation; generating instructions for activation and operation of an inhalation delivery device to provide the requested desired dose or amount based on the determined inhalation delivery device operating parameters; and transmitting the instructions to an ejector mechanism of an inhalation delivery device for execution at the inhalation delivery device to provide for activation and operation of the inhalation delivery device upon use to thereby control the dose and/or amount of the at least one agent or ingredient of a composition for delivery to the pulmonary system of user via inhalation.

In yet other aspects, a method of displaying historical data of use of an inhalation delivery device is provided. The method generally comprises receiving, at a user computing device from a user interface, a request for historical data associated with use of an inhalation delivery device to deliver an inhaled composition, the historical data comprising an element selected from: number of doses administered, dosages and amounts administered, average inhalation topography, and combinations thereof; transmitting, from the user computing device to an inhalation delivery device, the request for historical data; receiving, at the user computing device from the inhalation delivery device, the requested historical data; generating, at the user computing device, graphical data for rendering and displaying a report of the requested historical data; rendering the graphical data, at the user computing device; and displaying a report on a display of the user computing device, the report including graphical elements including the historical data.

In certain embodiments, the displaying of historical data of use of an inhalation delivery device facilities the cessation of use. The rendering of the graphical data may further include displaying changes in dosage amounts over time to illustrate reductions or increases in use of the inhalation delivery device.

In other embodiments, the method further comprises receiving a selection of a graphical element of the report at the user computing device; generating, in response to receiving the selection, additional graphical data related to the selected graphical element; rendering the additional graphical data, at the user computing device; and displaying a report on a display of the user computing device, the report including additional graphical data related to the selected graphical element. In certain embodiments, the report comprises education information related to cessation of use.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the detailed descriptions are to be regarded as illustrative in nature and not restrictive.

BRIEF DESCRIPTION OF THE DRAWINGS

FIG. 4A illustrates a linear relationship wherein no dosing occurs prior to a minimum threshold inhalation flow rate. FIG. 4B illustrates a non-linear relationship with an optimum inhalation range to facilitate delivery to the pulmonary system.

FIG. 4C illustrates a linear relationship wherein no dosing occurs prior to a minimum threshold inhalation flow rate along with a minimum dose rate. FIG. 4C illustrates a similar linear relationship wherein no dosing occurs prior to a minimum threshold inhalation flow rate along, with both a minimum and a maximum dose rate. FIG. 4E illustrates a non-linear relationship that escalates dose rate more quickly with inhalation rate. FIG. 4F illustrates a non-linear relationship that escalates dose rate more slowly with inhalation rate. FIG. 4G illustrates a step-wise increase in dose rate with inhalation rate.

FIG. 5A illustrates a 30% dose rate, while FIG. 5B illustrates an 80% dose rate.

Figure 1:
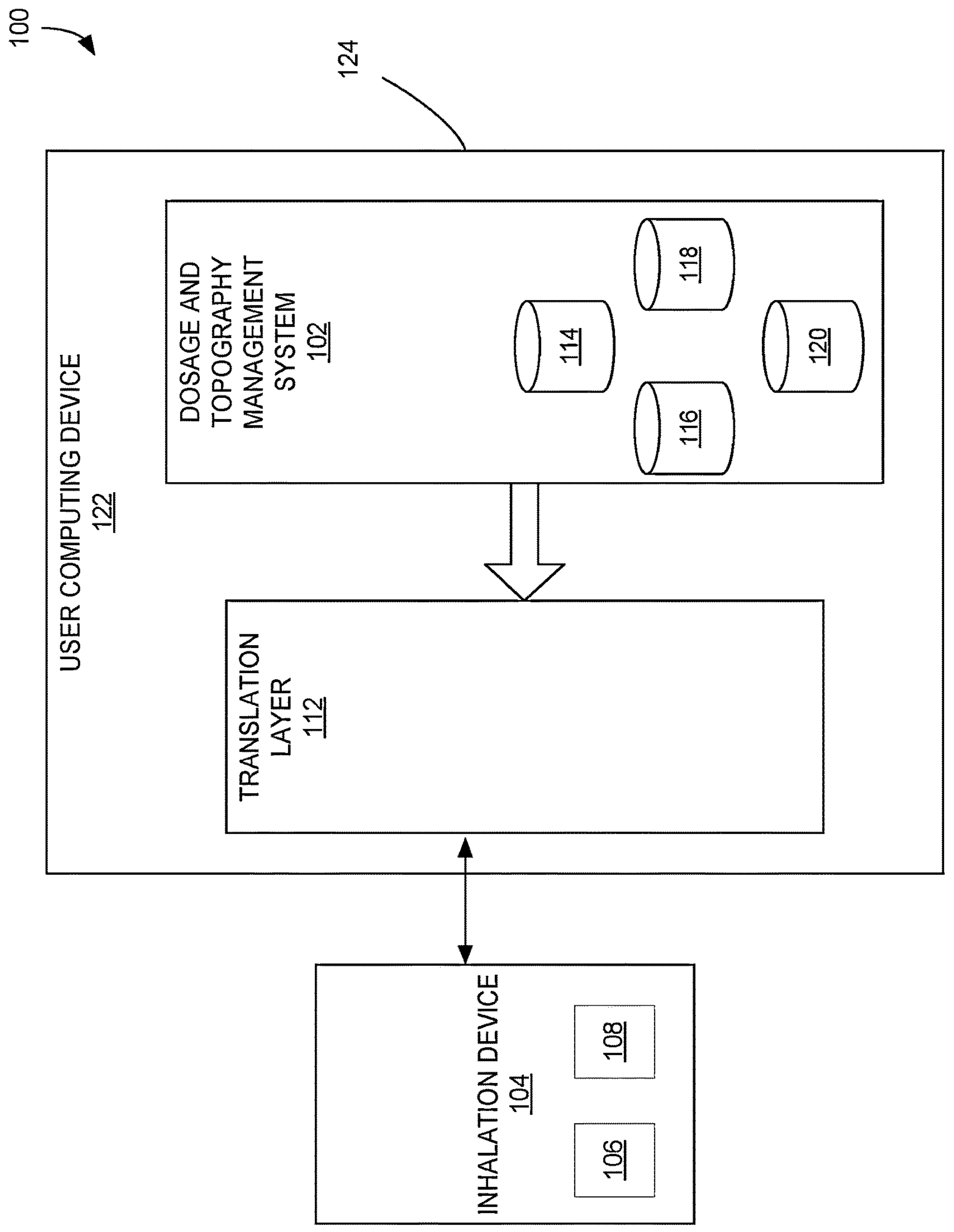
FIG. 1 is a block diagram illustrating an example lab result processing system, according to one embodiment of the disclosure.

The foregoing and other objects, features, and advantages of the present disclosure set forth herein will be apparent from the following description of particular embodiments of those inventive concepts, as illustrated in the accompanying drawings. Also, in the drawings the like reference characters refer to the same parts throughout the different views. The drawings depict only typical embodiments of the present disclosure and, therefore, are not to be considered limiting in scope.

DETAILED DESCRIPTION

To address these and other needs, methods, devices and systems are provided wherein compositions are delivered to the pulmonary system of an intended user via inhalation in a controlled manner and at a desired doses and/or amounts. In certain aspects, the methods, devices and systems deliver inhaled compositions in a manner so as to prevent misuse, to prevent overuse, to provide controlled cessation of use, or to provide other desired dosage and/or amount control or metering by the intended user or other third parties.

In certain aspects, the methods, devices and systems can improve human health through more effective use of inhaled compositions, including prescription drugs for Asthma/COPD and oncology; cannabis agents, including therapeutic medical marijuana; and nicotine agents. In certain embodiments, the methods, devices and systems provide for the delivery of inhaled compositions with reduced side effects, while allowing for controlled dosing and administration such that users may have improved control of use and inhalation topography. In certain embodiments, such improved control of use and inhalation topography may facilitate cessation efforts of various inhaled compositions, e.g., nicotine, controlled substances, etc.

In certain aspects, the methods, devices and systems allow for delivery of compositions to the pulmonary system of an intended user via inhalation at controlled dosages and/or amounts, e.g., within a desired dosage window and/or inhalation topography. In certain embodiments, the methods, devices and systems achieve a desired dosage or amount delivery via controlled dosage or amount metering. In certain embodiments, dosage windows and/or inhalation topography may be used, e.g., to provide for controlled cessation of use or to provide a desired therapeutic window.

Without being limited, in certain aspects, dosage and/or amount metering may provide a desired inhalation topography. As used herein, inhalation topography refers to the relationship between inhalation flow rate and dose/amount administered. The inhalation topography may be any desired relationship, e.g., zero order (i.e., no change in dose/amount administered with change in flow rate, once a minimum threshold flow rate is achieved); linear, non-linear, etc. In certain embodiments, a desired dosing regimen may also require more than one inhalation topography, selected based on the particular dose to be administered (e.g., initial dose, maintenance dose, morning dose, evening dose, add-on dose, "stress use" dose, etc.)

By way of non-limiting example, in certain embodiments, the inhalation topography may include an initial bolus dose and/or amount followed by maintenance dosing and/or amounts, so as to maintain a desired therapeutic dosage window or to provide controlled cessation of use. In other embodiments, the inhalation topography may include variations in dose/amount administration rate based on the time of day or trigger for use (e.g., morning use, day time use, night time use, "stress use", etc.). As explained in further detail herein, the methods, devices and systems of the disclosure uniquely allow for dosage and/or amount metering in a controlled manner so as to prevent misuse, to prevent overuse, to provide controlled cessation of use, or to provide other desired dosage and/or amount control or metering by the intended user or other third parties.

As will be recognized by those of skill in the art, desired dosing or administration, including desired therapeutic windows, will depend on the composition to be delivered and attributes of the intended user, including age, weight, sex, health, etc. By way of non-limiting example, dosing or administration may be based on a μg of agent/kg of subject weight basis, and may be refined based on the particular pharmacokinetics of the intended subject if desired.

In connection with the methods, devices, and systems discussed herein, inhalation delivery devices and systems are disclosed, which are capable of delivering a defined inhalation volume such that an adequate and repeatable high percentage of the droplets are delivered into the desired location within the airways, e.g., the mouth, throat, and/or alveolar airways, etc., of the subject during use. The inhalation delivery device and systems overcome limitations of the currently available inhalation devices and vapes, in part, by providing for metering of dosing and providing for desired inhalation topography and dosing regimens.

In certain embodiments, the methods, devices and systems of the disclosure may be used to deliver any suitable composition comprising one or more active agent or combination of active agents to the pulmonary system of a user. As generally understood, an active agent is any compound or substance that may exert a biological effect on a user when administered to the user. In the context of the present disclosure, such administration is via inhalation.

In certain aspects of the disclosure, the compositions to be administered may comprise one or more active agents in combination with one or more additives, flavorings or other excipients, formulated together as a single composition or as separate compositions for combination upon administration. As described in further detail herein, the methods, devices and systems of the disclosure may be used to provide for dosage and/or amount control and metering of the composition as a whole, of an one or more active agents, of one or more additives, flavorings, or other excipients, wherein the metering is simultaneous controlled for the entire composition, independently controlled by ingredient, or any desired allocation of control of dosage and/or amount of ingredient and combination thereof.

For example, the methods, devices and systems may be used to delivery compositions including therapeutic agents, such as small and large molecules. In certain embodiments, the methods, devices, and systems of the disclosure may be used to deliver compositions including active agents with a potential for abuse or overdose, such as nicotine and salts thereof, opioid analgesics, psycho-stimulants, cannabinoid agonists, dopamine agonists, steroids, and sedative hypnotics to the pulmonary system of an intended user via inhalation in a controlled manner which is only enabled by instructions from a doctor or pharmacy. In certain embodiments, the compositions may comprise additives, flavorings and other excipients, as desired. Again, such additives, flavoring, and other excipients may be formulated together with the active agent(s) as a single composition, or as separate compositions for combination upon administration.

In some embodiments, the methods, devices, and systems of the disclosure may be used to deliver a composition comprising nicotine or a salt thereof, e.g., including the water-nicotine azeotrope. By way of non-limiting example, the nicotine or salt thereof may be the naturally occurring alkaloid compound having the chemical name S-3-(1-methyl-2-pyrrolidinyl)pyridine, which may be isolated and purified from nature or synthetically produced in any manner, or any of its occurring salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, pyruvate, saccharate, benzoate, methanesulfonate, ethanesulfonate, benzenesulfonate, p-toluene sulfonate, camphorate and pamoate salts. In other embodiments, the composition may further include any pharmacologically acceptable derivative, metabolite or analog of nicotine which exhibits pharmacotherapeutic properties similar to nicotine. Such derivatives and metabolites are known in the art, and include cotinine, norcotinine, nornicotine, nicotine N-oxide, cotinine N-oxide, 3-hydroxycotinine and 5-hydroxycotinine or pharmaceutically acceptable salts thereof.

In certain embodiments, the methods, devices, and systems of the disclosure may be used to deliver a composition comprising one or more active agents that may isolated or derived from cannabis. For instance, the agent may be a natural or synthetic cannabinoid, e.g., THC (tetrahydrocannabinol), THCA (tetrahydrocannabinolic acid), CBD (cannabidiol), CBDA (cannabidiolic acid), CBN (cannabinol), CBG (cannabigerol), CBC (cannabichromene), CBL (cannabicyclol), CBV (cannabivarin), THCV (tetrahydrocannabivarin), CBDV (cannabidivarin), CBCV (cannabichromevarin), CBGV (cannabigerovarin), CBGM (cannabigerol monomethyl ether), CBE (cannabielsoin), CBT (cannabicitran), and various combinations thereof. In other embodiments, the agent may be a ligand that bind the cannabinoid receptor type 1 (CB1), the cannabinoid receptor type 2 (CB2), or combinations thereof. In particular embodiments, the agent may comprise THC, CBD, or combinations thereof. By way of example, the agent may comprise 95% THC, 98% THC, 99% THC, 95% CBD, 98% CBD, 99% CBD, etc.

In certain aspects, the methods, devices and systems of the disclosure may be used to deliver compositions including one or more active agents having the potential for abuse, e.g., including opioid analgesics, psycho-stimulants, cannabinoid agonists, dopamine agonists, steroids, and sedative hypnotics. By way of non-limiting example, opioid analgesics include, but are not limited to, morphine, heroin, hydromorphone, oxymorphone, buprenorphine, levorphanol, butorphanol, codeine, dihydrocodeine, hydrocodone, oxycodone, meperidine, methadone, nalbulphine, opium, pentazocine, propoxyphene, as well as less widely employed compounds such as alfentanil, allylprodine, alphaprodine, anileridine, benzylmorphine, bezitramide, clonitazene, cyclazocine, desomorphine, dextromoramide, dezocine, diampromide, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydroxypethidine, isomethadone, ketobemidone, levallorphan, levophenacylmorphan, lofentanil, meptazinol, metazocine, metopon, myrophine, narceine, nicomorphine, norpipanone, papvretum, phenadoxone, phenomorphan, phenazocine, phenoperidine, piminodine, propiram, sufentanil, tramadol, tilidine, and salts and mixtures thereof.

In other embodiments, the methods, devices and systems of the disclosure may be used to treat various diseases, disorders and conditions by delivering therapeutic agents to the pulmonary system of a subject. In this regard, the methods, devices and systems may be used to deliver therapeutic agents both locally to the pulmonary system, and systemically to the body. In certain embodiments, the therapeutic agent may include THC, CBD, or other cannabinoids for the treatment of epilepsy, seizures and other conditions.

In accordance with certain aspects of the disclosure, controlled dosages to achieve a desired inhalation topography or therapeutic dosage window may vary depending on the particular composition and therapeutic agent delivered to an intended user, and will also vary according to the age, body weight, and response of the individual user.

Suitable dosing regimens can be selected by those skilled in the art with due consideration of such factors. In general, daily dosages may range of from about 1 μg/kg to about 150 mg/kg per day. In certainly embodiments, a daily dose range may range from about 5 μg/kg to about 100 mg/kg per day, from about 8 μg/kg to about 90 mg/kg per day, from about 8 μg/kg to about 10 mg/kg per day, etc. In selecting desired dosing regimens and inhalation topography, dosing may be initiated at a lower dose, and increased if necessary, as either a single dose or divided doses, depending on the user's global response. Alternatively, in some instance, it may be desired to administer a larger initial bolus dose, followed by smaller maintenance doses. It may be necessary to use dosages of the composition outside the ranges disclosed herein in some cases, as will be apparent to those of ordinary skill in the art. Furthermore, it is noted that the skilled artisan will know how and when to interrupt, adjust, or terminate dosing in conjunction with individual user response.

By way of non-limiting example, the devices and systems of the disclosure may be configured to provide dose and/or amount metering at desired increments, e.g., 5 microgram, 10 microgram, 15 microgram, 20 microgram, 25 microgram, 30 microgram, 35 microgram, 40 microgram, 45 microgram, 50 microgram, etc. increments, to achieve a desired dose and/or amount. For instance, such incremental dosing may be used to achieve a desired dosage of, e.g., 1-1000, 10-500, 20-100, etc. microgram doses (e.g., at 10 microgram increments) per inhalation. As explained in further detail herein, the devices and systems of the disclosure may provide the desired dosing increments through actuation of an ejector mechanism for a designated duration of time.

In one embodiment, compositions may be administered as a single once-a-day dose. In another embodiment, compositions may be administered as divided doses throughout a day. As will be apparent, the methods, devices and systems of the disclosure provide for an efficient mechanism for providing administration of divided doses throughout the day in a controlled manner, e.g., to provide desired dosages and/or inhalation topography.

Certain aspects of the disclosure relate to a system for delivery of inhaled compositions to the pulmonary system of a user. In some embodiments, the system may include one or more inhalation delivery devices with dose metering capabilities, which may optionally interface with or communicate with one or more computing devices (e.g., wireless communication device, server, personal computer, etc.). In some embodiments, the systems of the disclosure include one or more inhalation delivery devices and one or more communication devices, wherein one or more of the inhalation delivery devices are interfaced with, or in communication with one or more of the computing devices. The systems of the disclosure provide substantial improvements over current inhaled delivery systems by improving dosing precision, dosing reliability, and delivery to the user. In certain embodiments, the systems of the disclosure include fully integrated monitoring capabilities designed to enhance dose metering and compliance.

In certain embodiments, the devices and systems may be configured to deliver droplets to various sites within the pulmonary system of the user, e.g., the mouth, throat, alveolar airways, etc. By way of example, for deposition in alveolar airways, droplets with aerodynamic diameters in the ranges of 1 to 6 μm are optimal, with droplets below about 4 μm shown to more effectively reach the alveolar region of the lungs, while larger droplets above about 6 μm are deposited in the mouth, on the tongue, or strike the throat and coat the bronchial passages. Smaller droplets, for example less than about 1 μm that penetrate more deeply into the lungs have a tendency to be exhaled. However, for certain agents and uses, droplets smaller than 1 μm for quick adsorption in the deep lung may be desirable, e.g., it may be desired to utilize droplets less than 4 μm, less than 2 μm, and less than 1 μm for the delivery of nicotine and related substances to the deep lungs.

In certain embodiments, the devices and systems may be configured to deliver droplets in a controllable and defined droplet size range. By way of example, the droplet size range includes at least about 50%, at least about 60%, at least about 70%, at least about 85%, at least about 90%, between about 50% and about 90%, between about 60% and about 90%, between about 70% and about 90%, etc., of the ejected droplets are in the respirable range of below about 4 μm, below about 3 μm, below about 2.5 μm, below about 2 μm, between about 0.7 μm and about 4 μm, between about 0.7 μm and about 3 μm, between about 0.7 μm and about 2.5 μm, between about 0.7 μm and about 2.0 μm, between about 0.7 μm and about 1.5 μm, between about 0.7 μm and about 1.0 μm, etc.

Certain embodiments of the disclosure may be configured to target multiple sites within the pulmonary system of user, e.g., the mouth (including the tongue) and the alveolar airways, as described in further detail herein. As explained in further detail herein, the devices and systems of the disclosure may deliver droplets to specific sites within the pulmonary system through the ejection of droplets of controlled droplet size(s).

In other embodiments, the devices and systems may be configured to deliver droplets having one or more diameters, relative to one another, such that droplets having multiple diameters relative to one another target multiple regions in the airways (mouth, tongue, throat, upper airways, lower airways, deep lung, etc.) By way of example, droplet diameters may range from about 0.7 μm to about 200 μm, about 0.7 μm to about 100 μm, about 0.7 μm to about 60 μm, about 0.7 μm to about 40 μm, about 0.7 μm to about 20 μm, about 0.7 μm to about 5 μm, about 0.7 μm to about 4.7 μm, about 0.7 μm to about 4 μm, about 0.7 μm to about 3.0 μm, about 0.7 μm to about 2.5 μm, about 0.7 μm and about 2.0 μm, about 0.7 μm and about 1.5 μm, about 0.7 μm and about 1.0 μm, about 5 μm to about 20 μm, about 5 μm to about 10 μm, and combinations thereof. In particular embodiments, at least a fraction of the droplets have diameters in the respirable range, while other droplets may have diameters in other sizes so as to target non-respirable locations (e.g., larger than about 5 μm). Illustrative ejected droplet streams in this regard might have 50%-70% of droplets in the respirable range (less than about 5 μm), and 30%-50% outside of the respirable range (about 5 μm-about 10 μm, about 5 μm-about 20 μm, etc.)

In other aspects of the disclosure, methods for generating an ejected stream of droplets for delivery to the pulmonary system of user using the devices and systems of the disclosure are provided.

As explained in further detail herein, in certain embodiments, the inhalation delivery devices of the disclosure may include a housing, one or more fluid reservoirs, one or more droplet ejector mechanisms, and a controller having a processor that may be programmed to provide the desired dosing increments. For instance, the processor may activate the ejector mechanism for a designated duration so as to eject droplets to achieve a desired dosing increment. The processor may be programmed in any suitable manner. In certain embodiments, the processor may be programmed by "reading" instructions from other device components (as explained in further detail herein); the microprocessor may be hard programmed at the factory, pharmacy or doctor's office; the processor may be programmed via a wireless interface from an external device (e.g., a smart device or other portable wireless device); the microprocessor may be programmed wirelessly from "cloud based" instructions; etc.

In certain aspects, the inhalation delivery devices of the disclosure may interface with or communicate with one or more computing devices (e.g., a wireless communication device such as a smart device or other portable wireless device, a server, a personal computer, etc.). In such embodiments, a user may interface with software or other applications (e.g., an App on a smart phone) to set a desired dose and/or amount level. In certain embodiments, a user may set different dose levels, e.g., depending on the time of day (e.g. a low dose at work and a higher dose in the evening or on weekends). Further, a user may set different dose and/or amount levels for different agents and/or ingredients. In yet other embodiments, preset dose limits may be programed into the device, e.g., into the controller, the ejector mechanism, the reservoir/ampoule, etc., such that the device may only dispense a certain number of doses per hour, per day, per month, etc. Such a feature may provide for tamper and/or abuse deterrent measures.

The foregoing and other aspects of the present disclosure will be discussed in further detail with reference made to the figures. FIG. 1 is a block diagram illustrating an example inhalation delivery system 100 in accordance with one implementation of the present disclosure. However, the embodiment illustrated in FIG. 1 is for illustrative purposes only, and does not limit the scope of the disclosure. For instance, the inhalation delivery device may comprise the dosage and topography management system, and may include various user interfaces (embodiment not shown).

In general, the system 100 includes a user computing device 122 that includes a dosage and topography management system 102 and an optional translation layer 122. The dosage and topography management system 102 facilitates retrieval of usage, dosage and device metrics, and other user information from one or more interfaced inhalation delivery devices 104, stores the retrieved data and information, determines inhalation delivery device 104 operating parameters, generates instructions for activation and operation of the inhalation delivery device 104, and generates and presents dosage control, usage and inhalation topography data, and associated information to users, such as through a user interface, website or other application API 124. The dosage and topography management system 102 may also provide data and instructions back to the inhalation delivery device 104 in response to input from the user via API 124 of computing device 122.

The dosage and topography management system 102 may be implemented in various ways, but may generally include software modules including programming instructions and code, executable via one or more processors of user computing device 122.

Data and information may be obtained by the dosage and topography management system 102 from and provided to one or more inhalation delivery devices 104. In general, the inhalation delivery device 104 may take various forms and communicate to the dosage and topography management system in various manners, e.g., Bluetooth, wifi, cellular, etc. But, in general, the inhalation delivery device 104 communicates with the user computing device to provide user data and user information to the dosage and topography management system 102, and the dosage and topography management system 102 can provide data and instructions back to the inhalation delivery device 104 in response to input from the users via user computing device 122. Any suitable wireless communication manner, e.g., a wireless communication chip/transceiver, Bluetooth chip, wifi chip, cellular chip, etc., may be used.

As data may be collected in various formats and using various protocols, certain implementations of the present disclosure may include an optional translation layer 112 configured to facilitate communication between the inhalation delivery device 104 and the dosage and topography management system 102 of the user computing device 122. In certain implementations, the translation layer 112 may include one or more software modules configured to communicate and receive data from one or more of the inhalation delivery device 104, and to convert the received data into a standardized format for storage and use by the dosage and topography management system 102. In certain implementations, the translation layer 112 may be implemented using a representational state transfer (REST)-based architecture. In other implementations, the translation layer 112 may instead be implemented using one or more remote procedure calls (RPC), web services (such as SOAP or WSDL), or other approaches for facilitating communication between computing devices and/or software modules.

The dosage and topography management system 102 may include, be communicatively coupled or otherwise have access to one or more databases or similar data stores. Such data stores are generally used to store information for use by the dosage and topography management system 102. For example, the system 100 includes each of a user information data store 114, an inhalation flow/dosage relationship data store 116, a physical properties data store 118, and a cessation of use platform data store 120.

The user information data store 114 may be populated with information regarding users of the system 100. Such information may include, without limitation, login credentials for users of the system and contact information. Information contained within the user information data store 114 may vary depending on whether the stored data corresponds to a laboratory or clinical user or a patient. The inhalation flow/dosage relationship data store 116 may include one or more linear or non-linear relationships between inhalation flow rate and dosage rate based on readings from internal device sensors to provide, e.g., duration of dose, etc. Similarly, the physical properties data store 118 may provide physical properties of compositions to assist with calculations of doses administered, doses remaining, concentrations, etc. The cessation of use platform data store 120 may provide preferred dosing regimens for desired cessation of use profile requests and/or content related to cessation of use. Such content may include text, images, videos, audio, or any other similar content that may be used to convey educational or other information to the user.

Although illustrated in FIG. 1 as distinct data objects, the data stores 114-120 may be implemented as more or fewer data objects and, as a result, the implementation illustrated in FIG. 1 is intended merely as a non-limiting example. For example, more or fewer data sources may be used to store data for use by the dosage and topography management system 102, and particular types of data may be stored or otherwise distributed across any number of data sources. In certain implementations, multiple data stores may be used to store the same data to provide redundancy, improved accessibility, or similar benefits. Moreover, while user information, data stores, and content are provided as specific examples of data that may be stored and accessible by the dosage and topography management system 102, it should be appreciated that other implementations of the present disclosure may include the storage, maintenance, and retrieval of other data that may be beneficial to users of the system 100.

It should also be appreciated that the data stores 114-120 are merely examples of databases or other data objects that may be used to implement the system 102. For example, in addition to the user, data and content discussed above, additional data objects may be implemented to facilitate other functions of the system. In other embodiments, fewer sources of data may be utilized.

As previously noted, the user computing device 122 may be any of a number of computing devices including, without limitation, a smartphone, a tablet, a smartwatch, a laptop computer, a desktop computer, or any other similar computing device. In certain implementations, the user accesses the dosage and topography management system 102 through an application, browser, or similar software executed on the computing device 122 and, in some instances, may be a mobile device that provides fast and easy access to the inhalation delivery device 104.

In certain aspects, the inhalation delivery device 104 includes a processor 106 which may be programmed to ensure timing and actuation of the ejector mechanism in accordance with desired parameters, e.g., based on the duration of piezoelectric activation to achieve desired dosages and/or amounts, etc. Processor 106 may be programmed at the factory, or it may receive instructions from user input via the inhalation control device 104 or the user computing device 122, as described herein. Dose counting and lockouts may also be preprogramed into the microprocessor or provided by user instructions from the inhalation delivery device or user computing device.

In certain embodiments, the inhalation delivery device 104 includes or interfaces with a memory 108 to record the date-time of each ejection event, as well as the user's inhalation flow rate during the dose inhalation to facilitate user monitoring, as well as reservoir usage monitoring. Although illustrated in FIG. 1 as being onboard the inhalation delivery device 104, inhalation delivery device 104 may alternatively communicate with a remote memory store, e.g., located within the user computing device (not shown).

Communication between the dosage and topography management system 102 and the user computing device 122 may be facilitate through one or more application programming interfaces (APIs) 124. In one example implementation, such APIs may rely on JavaScript Object Notation (JSON) or a similar standard to for transmission of data between the dosage and topography management system 102 and the user computing device 122, however, it should be appreciated that communication between the dosage and topography management system 102 and the user computing device 122 may occur using any of a number of communication protocols currently known or hereafter developed.

The API 124 may support a variety of functions to facilitate interaction between the dosage and topography management system 102, the inhalation delivery device 104, and the user computing device 122. The following examples are merely illustrative of functions and subroutines that may be included in the API 124 and should not be seen as limiting.

In one aspect, a user may log into the dosage and topography management system 102 by providing appropriate credentials, which may include one or more of a user name, a password, a multi-factor authentication code, biometric information (e.g., a face scan or fingerprint), or any other similar identifying information.

User authentication may also include authentication via the inhalation delivery device 104. In this regard, the inhalation delivery device 104 may include various biometric security components, e.g., fingerprint scanner, in connection with activation, lock/unlock, and interaction with the dosage and topography management system 102 to further authenticate user credentials. In certain embodiments, an inhalation delivery device 104 may be paired to one or more user computing devices 122 via the dosage and topography management system 102. For example, a inhalation delivery device 102 may be initialized and/or activated by a user via various biometric information (e.g., fingerprint). Upon initialization, the inhalation delivery device 104 may communicate with a user computing device 122 via a wireless communication network (e.g., Bluetooth, wifi, cellular, etc.) to pair with an application on the user computing device 122. Once paired, the dosage and topography management system 102 can facilitate further interactions between the inhalation delivery device 104 and the user computing device 122.

API 124 may be used to facilitate user authentication. Such an aspect may include functionality for authorizing a user, such as by verifying login and password information provided by the user. The API 124 may further support registration and pre-registration of a user, the latter including transmission and verification of an authorization number or similar verification token that may be transmitted to a user by text message, phone, or other communication method.

In other aspects, the disclosure relates to a methods, devices and systems which facilitate controlled dose and/or amount metering, e.g., to achieve desired inhalation topography for various compositions of the disclosure, such as cannabinoid compositions including THC and/or CBD, or nicotine compositions.

In other embodiments of the disclosure, a user may fine tune a dose/amount level based upon self-monitoring of their own internal state or perceptions to achieve a desired inhalation topography and/or therapeutic window. In certain embodiments, the dose/amount adjustments may include total dosage limits to aid in controlled cessation efforts. For example, total dosage limits per unit time may be set to allow for controlled, stepped-down total dosages while maintaining dose metering to thereby achieve desired dosage levels below the total dosage limits.

Without intending to be limited by theory, in certain aspects of the disclosure, there is a targeted window for effective dosing of agents of the disclosure such as cannabinoid including THC and/or CBD. For instance, too little of an amount does not provide effective pain relief, and too much may cause unwanted psychotropic effects or may cause the patient to feel unwell. Likewise, with nicotine dosing, there is often a targeted window of desired dosing of a user to provide desired outcomes with minimal side effects, particularly during cessation efforts. Like many pharmaceuticals, effective administration may require a larger, initial bolus dose to establish a desired blood level, followed by subsequent smaller doses to maintain the desired level in the blood. The methods, devices and systems of the disclosure allow for controlled dose and/or amount metering to achieve a targeted window of administration.

With such agents, effective dosing is often most accurately monitored and regulated by the patient's own perception and experience. For instance, this may be demonstrated by regular users who first take one or more long, deep inhalations typically followed by shorter, slower inhalations to reach a satisfactory dosage level. The shorter and slower inhalations result in a smaller amount of substance reaching the user.

Figure 2A:
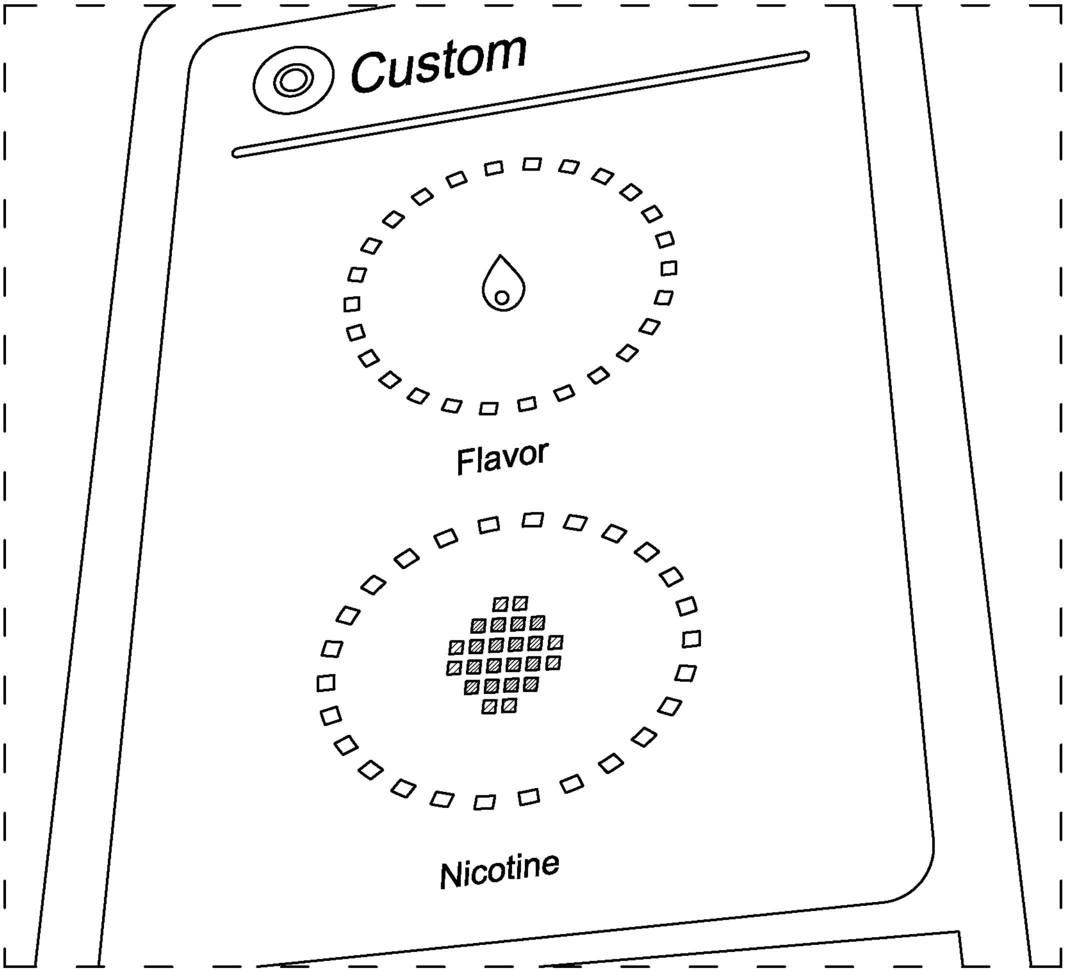
FIGS. 2A-2B are exemplary user interfaces that may be provided through a dosage and topography management system, as illustrated in FIG. 1.

API 124 may further facilitate advanced functionality of the inhalation delivery device 104. For example, as illustrated in FIG. 2A, API 124 may provide a user interface to easily adjust and select independently controlled and metered active agent (e.g., nicotine) and flavor levels. The dosage and amount levels may be selected in any suitable manner, e.g., by increment (a designated selection of 10 increments, a designated selection of 20 increments, a designated selection of 40 increments, a designated selection of 50 increments, etc.), a designated concentration of agent/ingredient, a designated weight of agent/ingredient, etc. Based on input to API 124 regarding the requested dosage and/or amount levels, dosage and topography management system 102 may then interface with inhalation delivery device 104 and provide instructions to inhalation delivery device 104 to adjust delivery of the composition(s) accordingly. Alternatively, the inhalation delivery device 104 may include a dosage/amount adjustment interface to control dose and/or amount metering directly from the inhalation delivery device 104. Such an interface may include, e.g., toggle buttons, an LCD touchscreen, voice recognition, or any other suitable mechanism known in the art.

Figure 2B:
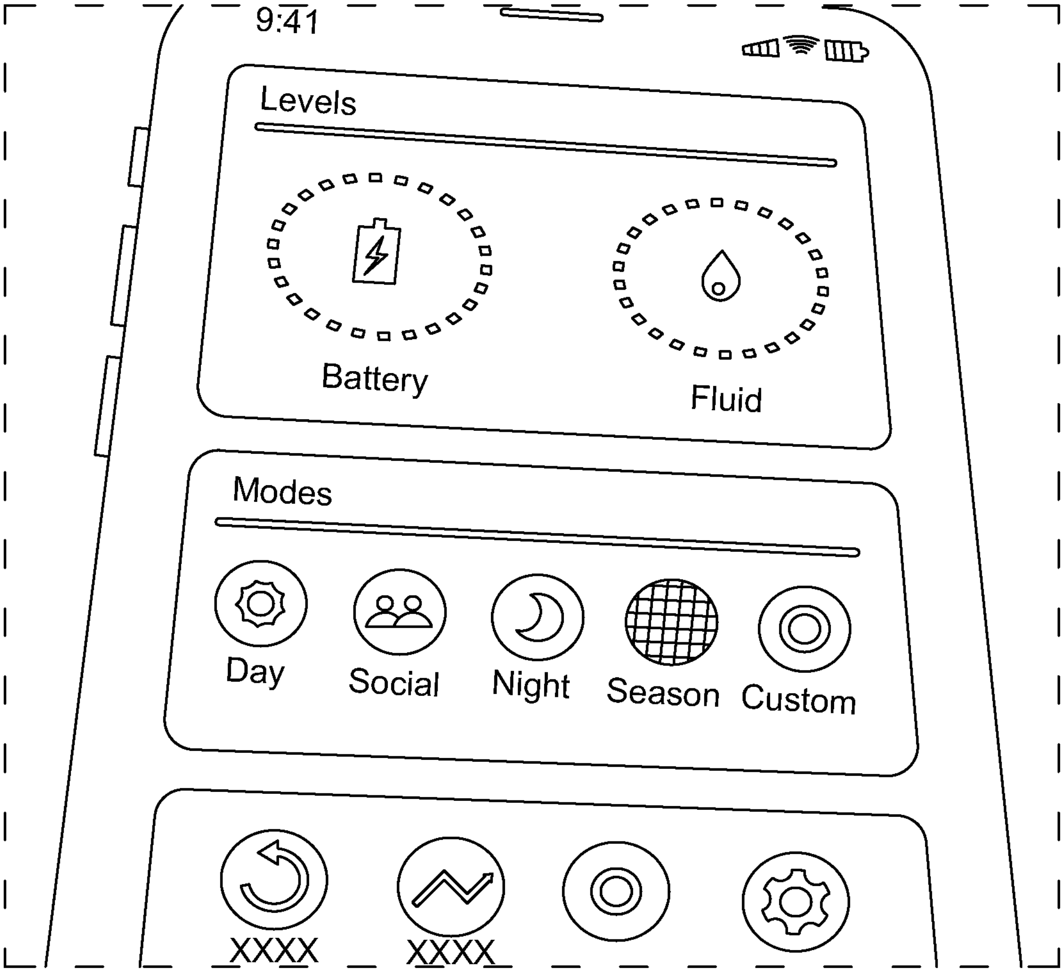

API 124 may provide yet additional advanced user interface and functionality to facilitate dose and amount metering. For example, with reference to FIG. 2B, multiple pre-programed and/or customizable use modes may be provided and selectable by a user. In certain embodiments, such use modes may provide for varied dosage and/or amount metering tuned to particular environments, uses, times of day, etc. By way of non-limiting example, use modes may include: day, social, night, stealth, custom, etc. Each use mode may be configured with differentiated agent (e.g., nicotine, THC, CBD, etc.) and additive/flavor levels. Without intending to be limited, stealth mode may be configured to allow for independent dose/amount adjustment for the agent (e.g., nicotine, THC, CBD, etc.) and flavor such that no perceivable vape "smoke" or aerosol is generated. Day mode be configured to provide higher dosage amounts of the agent (e.g., nicotine, THC, CBD, etc.), while night mode may be configured to provide lower dosage amount of the agent—or vice versa. A social mode setting may provide moderate dosage amounts of the agent and moderate amounts of the additives/flavors, so as to provide a less invasive user and third party experience.

Figure 3:
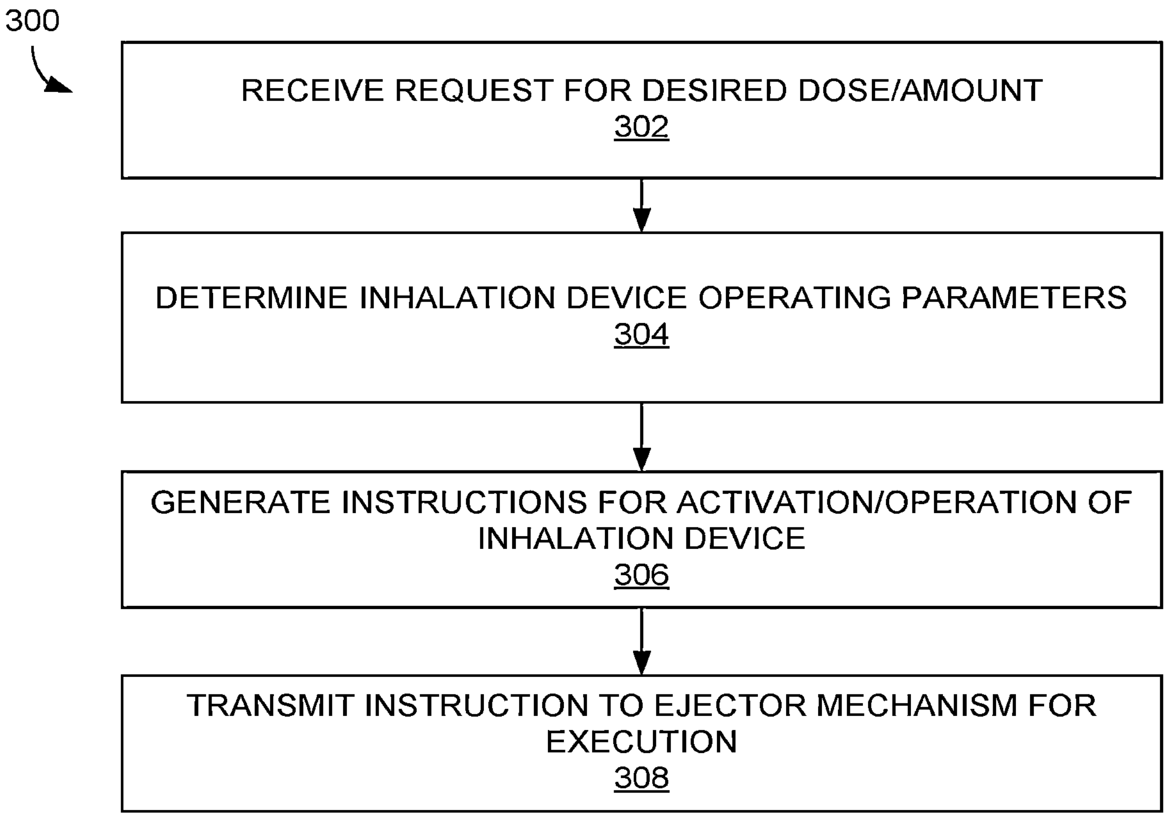
FIG. 3 is a flow chart illustrating a method for controlling the dose and/or amount of a composition for delivery to the pulmonary system of a user via inhalation, according to one embodiment of the disclosure.

For example, with reference to FIG. 3, a flow chart illustrating an exemplary method 300 for controlling the dose and/or amount of a composition for delivery to the pulmonary system of a user via inhalation is provided.

For purposes of the following example implementation and to provide context, reference is made to the various system elements of the lab result processing system 100 of FIG. 1. For example, method 300 will generally be described as being executed by the dosage and topography management system 102, the user computing device 122, and/or the inhalation delivery device 104, and of FIG. 1. It should be appreciated, however, that any reference to elements of FIG. 1 should be regarded as examples only and implementations of the present disclosure are not necessarily limited to the specific elements, architecture, etc. of the system 100 of FIG. 1.

By way of example, with reference to FIG. 3, method 300 relates to a method for controlling the dose and/or amount of a composition for delivery to the pulmonary system of a user via inhalation, from the perspective of computing system. In certain embodiments, the computing system may comprise the user computing device 122 and/or the inhalation device 104. In a first step, a request for a desired dose or amount of at least one agent or ingredient of a composition for delivery to the pulmonary system of a user via inhalation is received, at a computing system, e.g., user computing device 122 and/or an inhalation delivery device 104, based on user input (operation 302). The user input may be received via a user interface, e.g., API 124, or based on user action, e.g., input from inhalation flow rates during use.

In certain embodiments, the request for a desired dose or amount of at least one agent or ingredient of a composition may be received at the inhalation delivery device 104, as described herein. In such embodiments, the request may be transmitted from the inhalation delivery device 104 to the user computing device 122 for processing. In other embodiments, the inhalation delivery device may have preset, executable instructions for certain dosage requests, and may be to adjust and meter dosing without communication or interaction with the user computing device 122.

In other embodiments, rather than using controls via API 124 or the inhalation delivery device 104, a user may regulate dosing and amount metering by controlling inhalation flow velocity during use, which in turn regulates the total amount delivered via controlling the rate and duration of activation of the ejector mechanism of the device. Such fine dosage adjustments may be used to provide desired dose monitoring and inhalation topography, including, e.g., controlled cessation of use.

In response to receiving the request, the computing system determines, e.g., via dosage and topography management system 102, inhalation delivery device 104 operating parameters to provide the requested desired dose or amount of at least one agent or ingredient of a composition for delivery to the pulmonary system of a user via inhalation (operation 304). Such operating parameters may be any suitable inhalation delivery device operating parameters to achieve the desired dosage/amount. In certain embodiments, as described herein, operating parameters may include the duration of activation of a piezoelectric actuator of the inhalation delivery device. Suitable activation times may be determined, e.g., based of ejection time/dosage curves and related physical data that may be stored in the memory of dosage and topography management system 102.

The computing system then generates computer executable instructions for activation and operation of the inhalation delivery device 104 to provide the requested desired dose or amount based on the determined inhalation delivery device operating parameters (operation 306), and the computer executable instructions are transmitted to an ejector mechanism of the inhalation delivery device 104 (operation 308) for execution at the inhalation delivery device to provide for activation and operation of the inhalation delivery device upon use to thereby control the dose and/or amount of the at least one agent or ingredient of a composition for delivery to the pulmonary system of user via inhalation.

As described herein, in certain embodiment, methods, devices and systems are provided which allow for "hands free" dosing/amount metering. In certain embodiments, a user does not need to select a dosage amount on a user computing device or via buttons or a user interface on the inhalation delivery device. Instead, dose/amount metering may be controlled by the user according to the duration and/or intensity of inhalation flow. In certain embodiments, control of dose/amount metering based on the length and/or intensity of inhalation flow rate may be accomplished by monitoring inhalation flow via a pressure or flow sensor in the inhalation delivery device.

In some embodiments, inhalation topography, including maximum dosage/amount or the relationship between inhalation flow rate and duration can be defined, set or modified via the user computing device or inhalation delivery device in a similar manner to that described above with respect to dose/amount control. By way of non-limiting example, various zero order, linear, non-linear, step-wise, and other known relationships between inhalation flow rate and dosage may be uploaded to the inhalation delivery device, e.g., via the API of the user computing device. These relationships can then be used by the inhalation delivery device to adjust dose/amount metering based on inhalation flow rates.

Figure 4A:
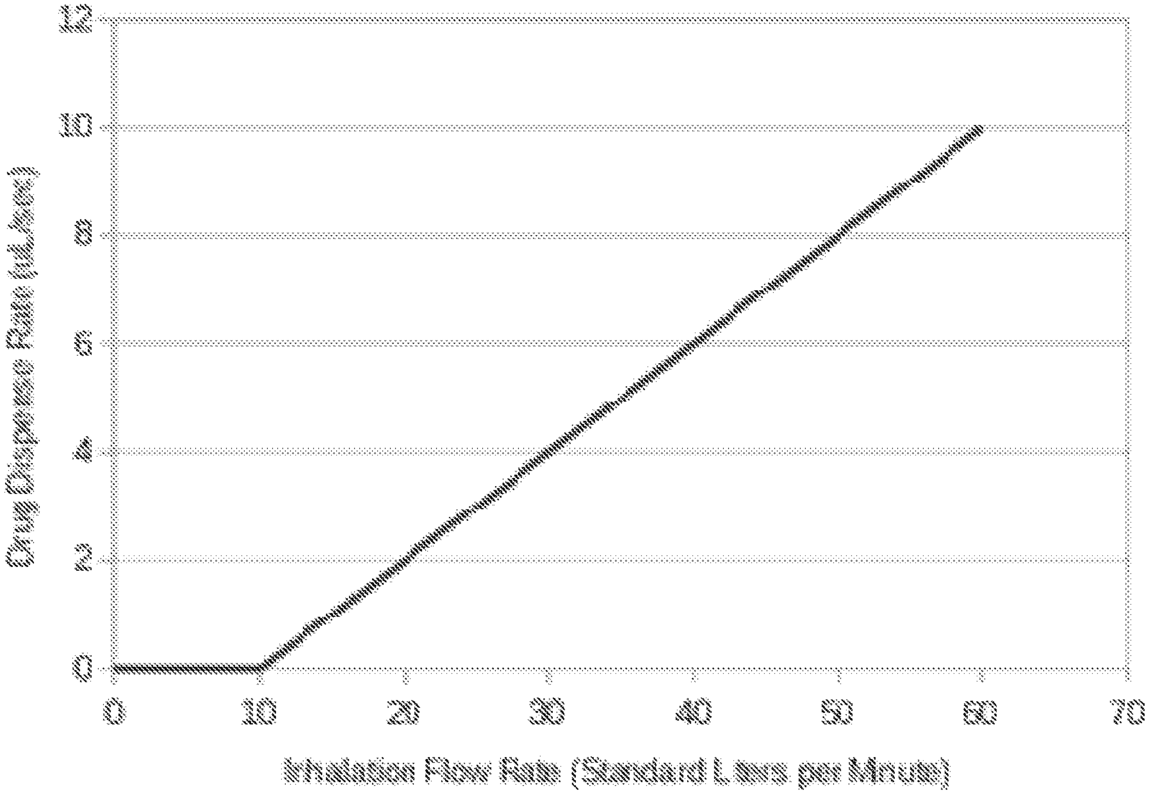
FIGS. 4A-4G illustrate exemplary inhalation topographies, in accordance with embodiments of the disclosure.

FIGS. 4A-4G illustrate exemplary inhalation topography relationships between inhalation flow rate and composition dispense rate (dose/amount metering). For example, with reference to FIG. 4A, a linear relationship is illustrated showing, e.g., an inhalation rate is 60 SLM (Standard liters per minute) dispensing a maximum dispense rate, e.g., 10 uL per second. At inhalation rates the dosage rate may decrease in a linear. For example, at 30 SLM the dosing rate may be 4 uL per second. As shown in FIG. 4A, at a very small inhalation flow rate, the dosing rate can cut off so that an inhalation flow rate less than, e.g., 10 SLM the composition dispense rate would be 0. Thus when a user wants a lower dosage, they can simply reduce the rate and/or duration of their inhalation. An additional benefit to a system that ceases droplet dispense when inhalation rates drop below a minimum level is the prevention of waste when a user only wants a very small dose and takes only a short inhalation.

Figure 4B:
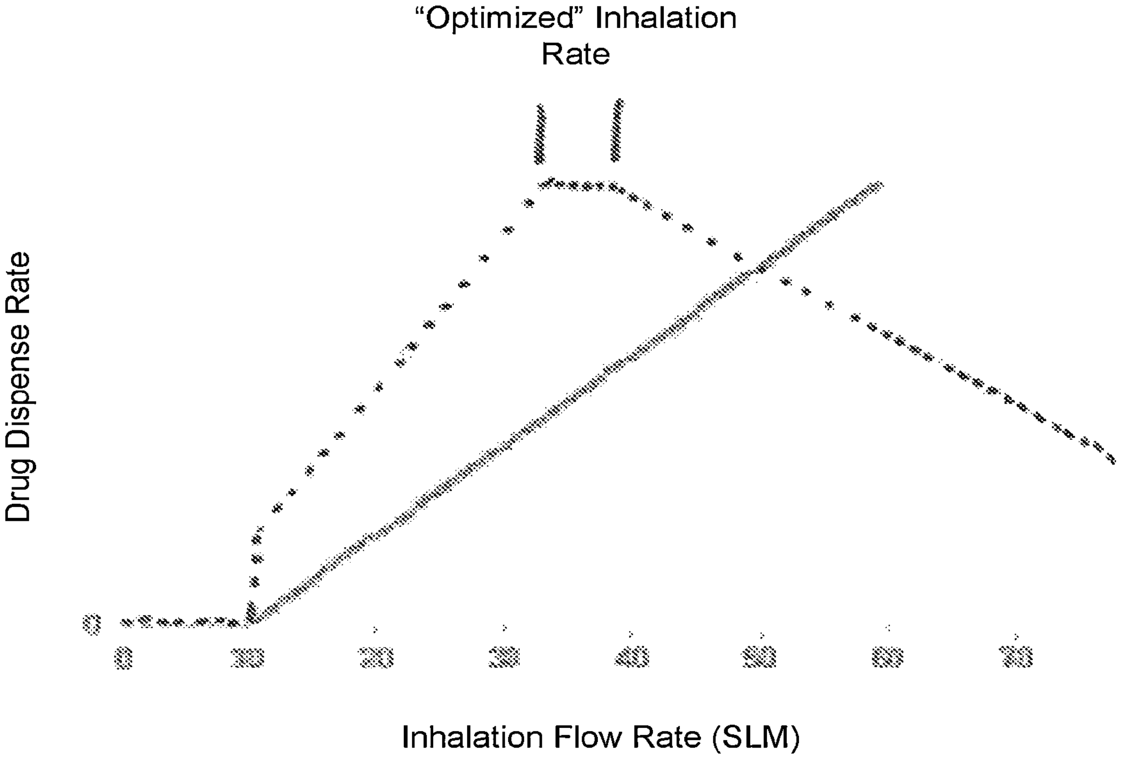

Examples of alternative relationships between inhalation flow rate and dispense rate are shown in FIGS. 4B-4G. By way of example, FIG. 4B illustrates a non-linear relationship which encourages the user to inhale more slowly to allow better deposition in the lung. To encourage slower inhalation, the maximum droplet dispense rate may be set to saturate at a preset optimal flow rate for droplet deposition in the lung. For inhalation flow rates above or below an optimal band of flow rates, dosages might be less (or more), to "train" the user to the optimal flow rate. Such training could be supported by lights or voice messages from the inhalation delivery device or user computing device, instructing and supplying feedback to the user.

Figure 4C:
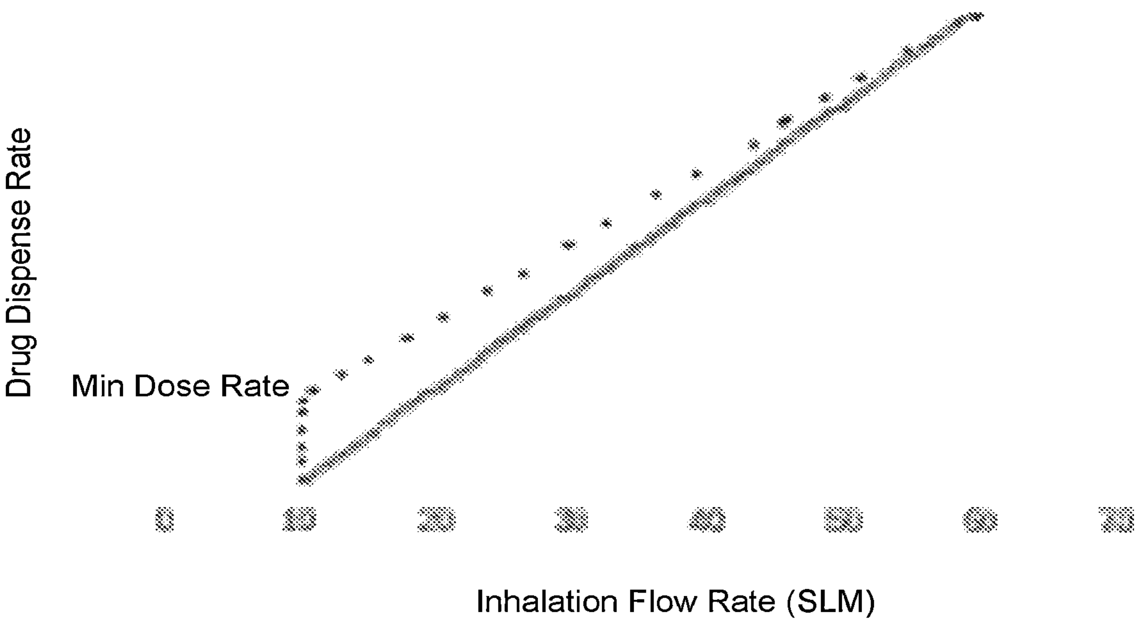
Figure 4D:
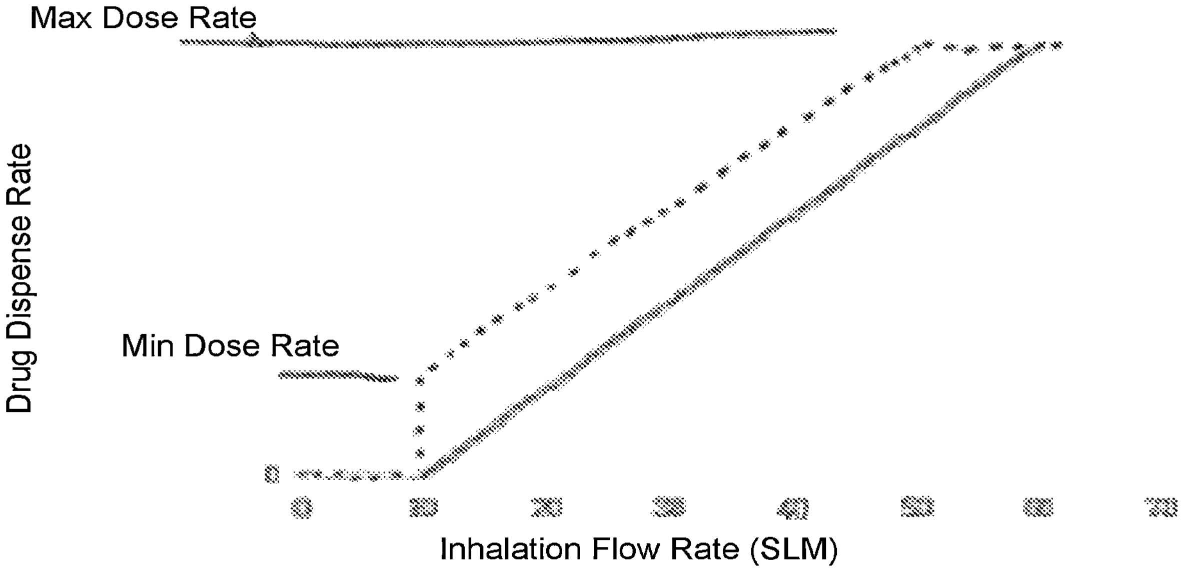
Figure 4E:
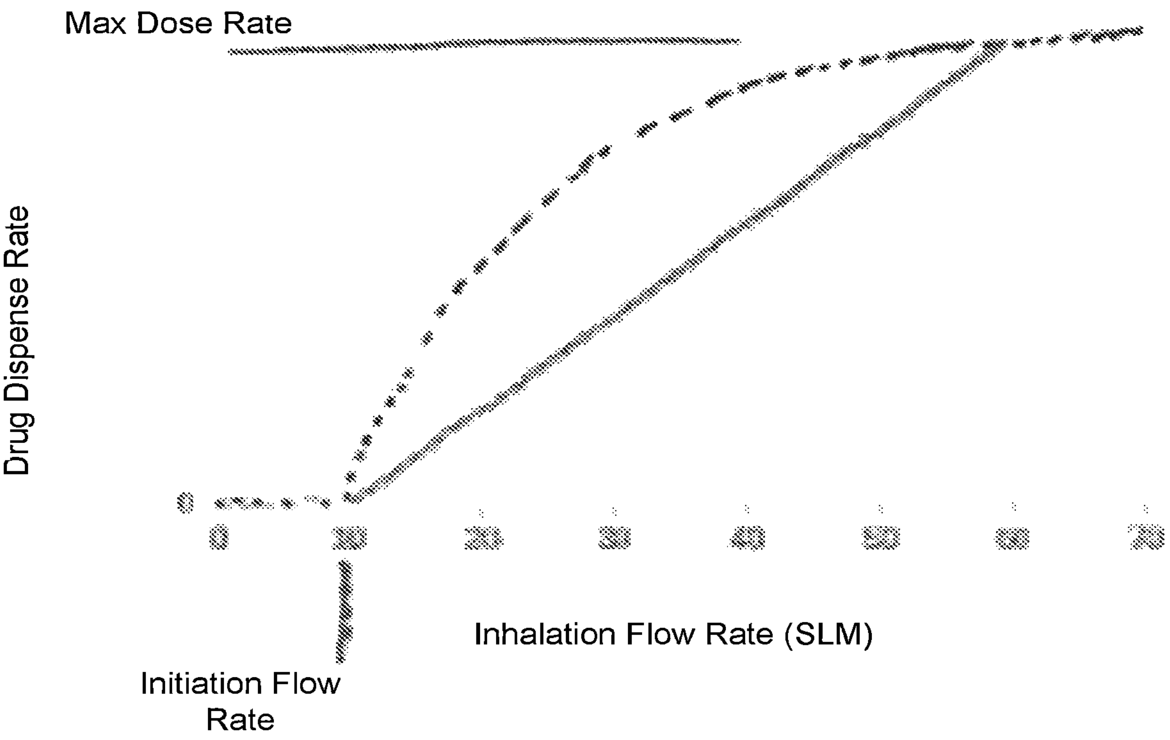
Figure 4F:
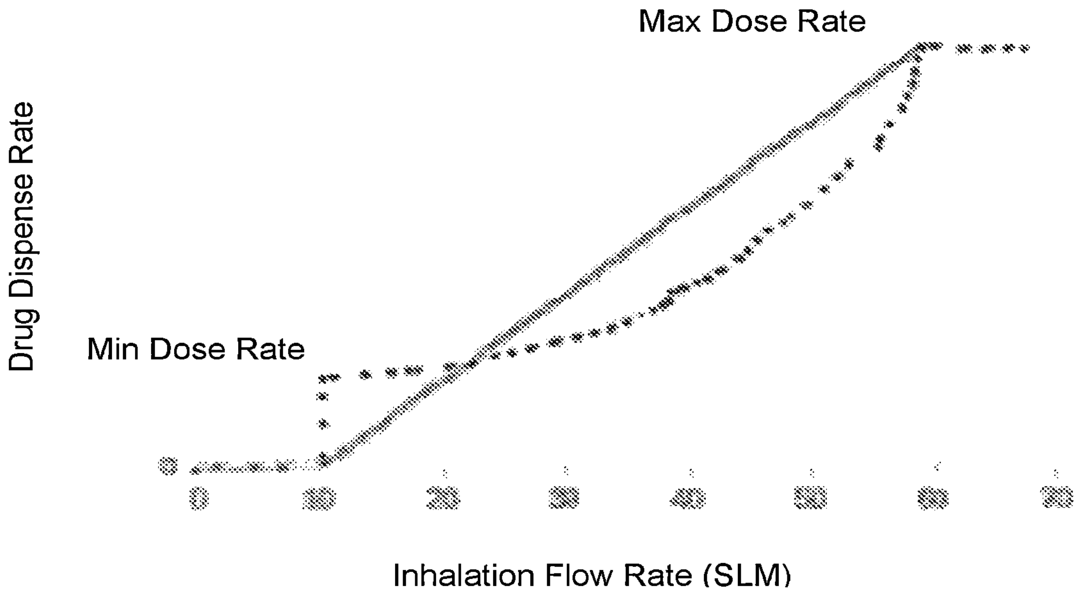
Figure 4G:
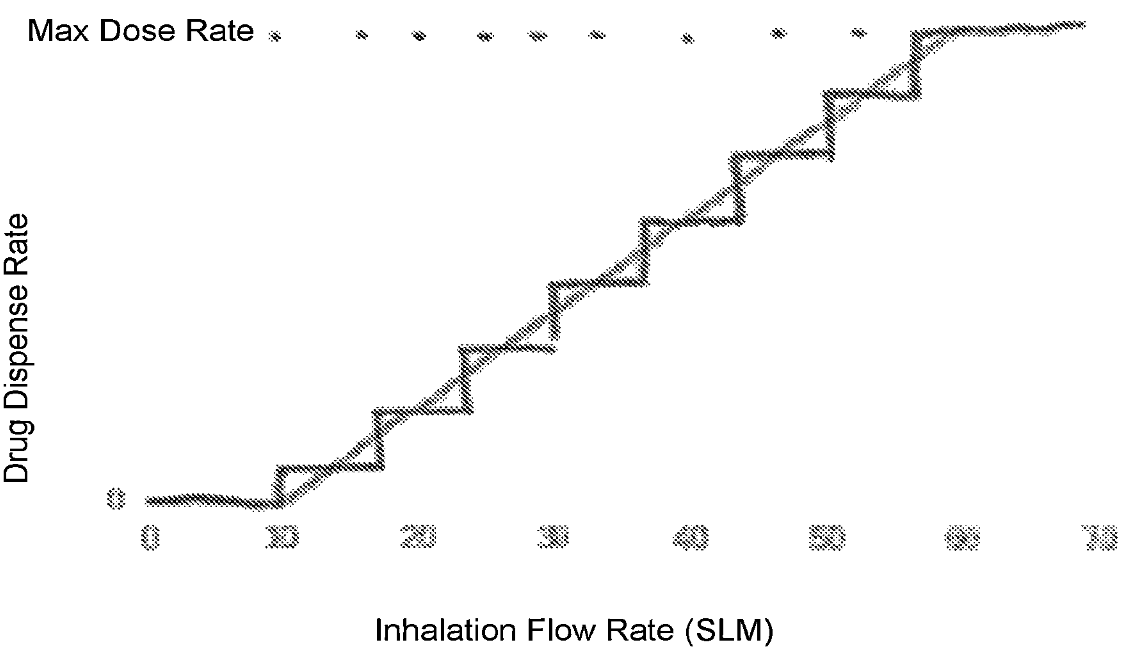

FIGS. 4C, 4D, 4E, 4F, and 4G each illustrate various relationships between inhalation flow rate and agent dispense rate. FIG. 4C shows a simple relationship wherein dosing is not initiated until a minimum threshold inhalation flow rate is achieved, and then dosing is initiated at a preset minimum dose rate. FIG. 4D shows a similar relationship, however the relationship includes a preset maximum dose rate. FIGS. 4E and 4F illustrate non-linear relationships with preset minimum and maximum dose rates, with FIG. 4E showing a relationship that provides more quickly escalating dosing with increased inhalation flow rates and FIG. 4F showing more slowly escalating dosing with increased inhalation flow rates. FIG. 4G illustrates a step wise increasing relationship with a preset maximum dose rate.

Figure 5A:
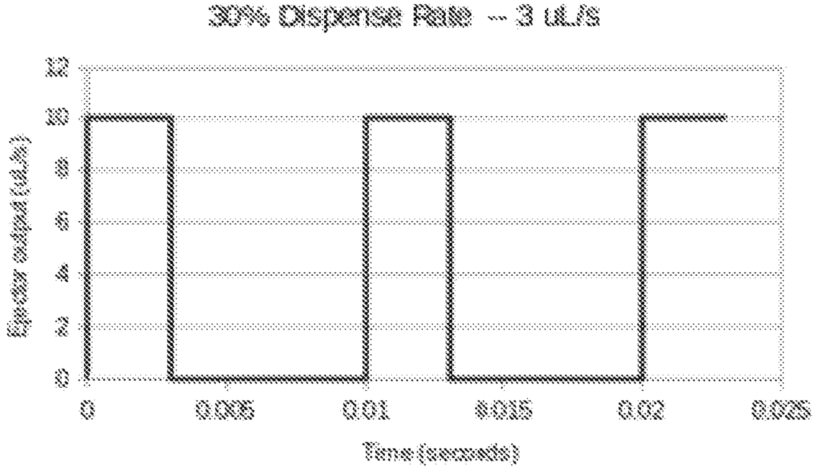
FIGS. 5A-5B illustrate the use of micro-strops in ejection activation to achieve desired dosing rates, in accordance with embodiments of the disclosure.
Figure 5B:
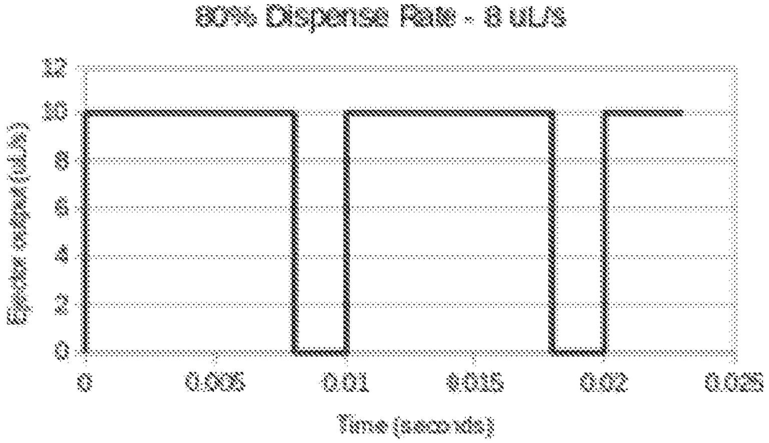

In certain embodiments, dispense rate may be controlled by placing micro-stops (non-active ejection times) in a continuous dispense. At flows below a preset level (10 SLM in this case), no ejection will occur. As shown in FIGS. 5A and 5B, by turning the ejector on and off in short time intervals, an average dispense rate less than the maximum dispense rate may be achieved—in a manner similar to Pulse Width Modulation used to control electrical actuators. To achieve the ejection rates described, the high frequency driving of a piezo actuator may be turned on and off according to the defined output pattern. For example, an ejector plate that dispenses at a continuous rate of 10 uL per second (microliters per second) can have a dispense rate of 5 uL per second by ejecting for 0.01 second and then pausing for 0.01 second. FIGS. 4A and 4B illustrate activation sequences to achieve 3 uL (30% dispense rate) and 8 uL (80% dispense rate). Ejection systems such as piezo-driven meshes where driving signals are typically about 100 kHz can easily accomplish this form of dispense control. Because a piezo system typically is driven at resonance and may require 10 to 100 cycles to reach full resonance, it some embodiments, the microprocessor may be programmed to provide error correction for any lack of ejection at the start of micro dispenses.

In some cases, a user may want a dispense duration that is fixed to permit the final part of their inhalation, after dispense has stopped to transport the composition into the lung. For example, dispense duration may be limited to 1 second so that a 2 second inhalation will transport the entire bolus to the lungs. In such a case, substance dispense would cease at one second, or when inhalation flow rate drops below a preset level.

Without intending to be limited, due to the ability to sense user inhalation flow rates and adjust or activate dose/amount metering based on inhalation rates, the methods, devices and systems of the disclosure have additional benefits including, e.g., allowing a user to control dosage and/or amount metering; avoiding waste from dispensing while a user is no longer effectively inhaling; allowing user adjustment or presetting of dispense rates to fit inhalation patterns or preferences; preventing second-hand "smoke" due to a device continuing to dispense droplets into room air without the user inhaling; avoiding the need for the user to time a dispense with their inhalations; preventing unauthorized user access (e.g., a child) by requiring a minimum inhalation rate before starting any ejection (e.g., small children are not able achieve the required inhalation flow rates to activate dispense).

API 124 may also provide additional functionality to a user, e.g., by providing notifications and information regarding battery life, reservoir fill status, dose counts and use levels (e.g., cigarette equivalent of nicotine consumed), etc. In other aspects, a user may access historical usage reports through the user interface. Results may be arranged, for example, in reverse chronological order and the user may click or otherwise select any of the listed results to "drill-down" and receive additional data and information.

In accordance with certain aspects of the disclosure, the systems of the disclosure provide a reliable monitoring system that can date and time stamp actual delivery of compositions, including doses and amounts delivered, e.g., to benefit users through self-monitoring or through involvement of care givers and family members. As described in further detail herein, the inhalation delivery device of the disclosure may detect inspiratory airflow and record/store inspiratory airflow in a memory (on the inhalation delivery device and/or a user computing device). The number of times that delivery is triggered may be incorporated and displayed via a dose counter on the inhalation delivery device and/or the API 124 of the user computing device 122.

In some embodiments, the inhalation delivery device and/or the user computing device, e.g., via the processor and memory, can monitor doses administered and doses remaining in a particular reservoir. In certain embodiments, the reservoir may comprise components that include identifiable information, and the inhalation delivery device may comprise components that may "read" the identifiable information to sense when a reservoir is inserted into the inhalation delivery device, e.g., based on a unique electrical resistance of each individual ampoule, an RFID chip, or other readable microchip (e.g., cryptoauthentication microchip).

In yet other aspects of the disclosure, the methods, devices and systems include:

Personal identification for activation—methods, devices and systems of the disclosure can also include personal identification keys to prevent unauthorized activation of the device, and delivery of the composition to someone other than the intended user. In certain embodiments, the personal identification key could include, e.g., activation in only specified locations identified via onboard GPS; authentication via PKI, blockchain PKI or similar public key authentication methodologies; biometric authentication, e.g., via onboard fingerprint recognition or facial recognition; tethering to user computing device (e.g., smartphone or smart-device) with biometric authentication, e.g., fingerprint or facial recognition, such that the user computing device sends an activation signal to the inhalation delivery device upon user authentication.

Authentication based lock-outs—methods, devices and systems of the disclosure include the ability to deliver a composition with a pre-determined "lock-out" setting based on, e.g., dosage amount, dosing regimen, expiration date, or other information indicative of tampering, misuse or overuse, which "lock-out" setting renders the associated reservoir and/or device inactive or inoperative, either on a permanent basis or temporarily until a pre-set amount of time has passed (e.g., to prevent overdose). In certain embodiments, the reservoir may be configured as a smart ampoule to include a readable chip, processor with memory, or other suitable mechanism to allow identification/activation information to be incorporated into a user specific smart ampoule such that the ampoule is identifiable to the lock-out settings.

Tamper resistance—methods, devices and systems of the disclosure also include tamper-resistant reservoirs, configured to reduce tampering and misuse of the compositions housed within the reservoir and tampering or misuse of the physical ampoule itself. In certain embodiments, the reservoir may be configured such that, if punctured or opened, the composition housed within the reservoir is rendered useless by abuse deterrent agents, e.g., polymers, gelling agents, and/or antagonist, etc., integrated into the structure of the reservoir. In other embodiments, the inhalation delivery devices and/or reservoirs may be configured to detect physical tampering of the reservoir, chemical or physical tampering of the composition, and/or a combination thereof. If such tampering is detected, the reservoir, inhalation delivery device, and/or user computing device may render the composition housed within the reservoir useless and/or deactivate the inhalation delivery device—either permanently or temporarily until a non-tampered reservoir is detected.

Cessation of use—methods, devices and systems of the disclosure provide for controlled cessation of use and related methods of monitoring to facilitate cessation of use. In certain embodiments, a desired dosage or amount of delivery may be achieved via controlled dosage or amount metering. The dosage or amount may be gradually reduced at predetermined intervals and by predetermined amounts based, e.g., on user input so as to achieve an overall reduction or cessation of use. By way of non-limiting example, the dosage or amount may be gradually reduced in stepwise manner over a set number of days, weeks or months, e.g., 5%, 10%, 25%, 50%, 75% reduction of dose per actuation, per day, per week, per month, etc., again, based on user input and desired timeframes for overall reduction or cessation of use. In other aspects, controlled dosage or amount metering may be adjusted at predetermined time intervals and amounts to as to provide increased amounts during times of increased "use stressors" (e.g., in the morning, at work, during commute time), with reduced doses and amounts at other times. Such adjustments may be used alone or in combination with gradual reductions in dose/amount, so as to provide an overall reduction in use. The methods devices and systems may also provide user monitoring features to facilitate cessation of use, e.g., monitoring and display of device usage and metrics information.

Figure 6:
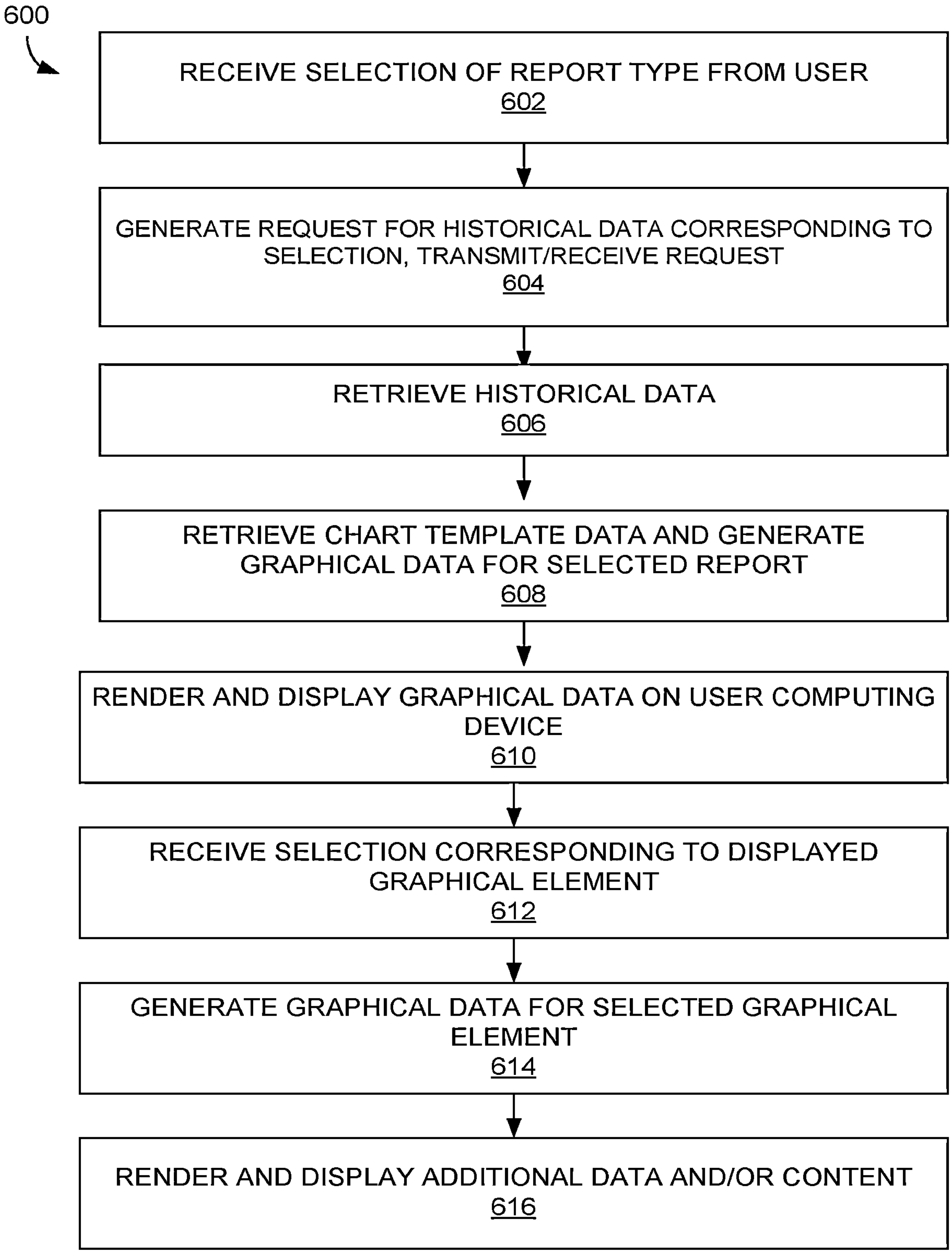
FIG. 6 is a flow chart illustrating a method for requesting and displaying graphical data, according to one embodiment of the disclosure.

For example, with reference to FIG. 6, a flow chart illustrating an exemplary method 600 for displaying device usage and metrics information to a user, e.g., to assist in cessation of use efforts is provided.

For purposes of the following example implementation and to provide context, reference is made to the various system elements of the lab result processing system 100 of FIG. 1. For example, method 600 will generally be described as being executed by the inhalation delivery device 104, the user computing device 122, and the dosage and topography management system 102 of FIG. 1. It should be appreciated, however, that any reference to elements of FIG. 1 should be regarded as examples only and implementations of the present disclosure are not necessarily limited to the specific elements, architecture, etc. of the system 100 of FIG. 1.

More specifically, the method 600 generally includes the steps for requesting and presenting inhalation delivery device usage data, including dosage and amount information. The method 600 may be executed, for example, by a server or similar central computing system (e.g., the dosage and topography management system 102 of FIG. 1) to generate charts for display on a user computing device (e.g., the user computing device 122 of FIG. 1). Method 600 may further include additional steps directed to the request and provision of reporting and/or educational content that extend beyond steps directed to generating and displaying historical data.

Beginning at operation 602, the user computing device 122 receives a selection of a device usage/metric report from a user. For example, the user computing device 122 may execute an application (or "app"), program, website, or other software that presents a user interface to a user of the user computing device 122.

In at least certain implementations, the user interface may present a user with a list of available report types, e.g., doses administered over last 24 hours, last 7 days, last 30 days, last 60 days, etc.; charting of changes in dosing over last 7 days, last 10 days, last 30 days, last 60 days, etc., charting of average inhalation topography profile over last 7 days, last 10 days, last 30 days, last 60 days, etc. In such implementations, receiving a selection at the user computing device 122 may be the result of the user selecting one of the displayed report types (e.g., by tapping or clicking one of the displayed report types). In other implementations, selecting a report type may include navigating to a page or similar portion of the user interface configured to display report results for available report types.

Regardless of how a selection is made, the user computing device 122 then generates and transmits a corresponding request for historical data to the dosage and topography management system 102 (operation 604) and or inhalation delivery device 104, depending on the location of the stored data.

The request received by the dosage and topography management system 102 and/or inhalation delivery device 104 may include, among other things, one or more of an identifier of the user in question and an identifier corresponding to the particular report type for which results are to be retrieved. In response to receiving the request and based on the contents of the request, the dosage and topography management system 102 and/or inhalation delivery device 104 retrieves the relevant historical data corresponding to the request (operation 506). If the data is located in the memory of the inhalation delivery device, the data is transmitted back to, and received by the dosage and topography management system 102 (not shown).

The dosage and topography management system 102 may also retrieve chart template data associated with the report type and generate the graphical data for generating the requested report (operation 608) for use in generating a graphical representation of the historical test result data. In general, chart templates include various values and parameters for related to the overall layout and style of a chart associated with the test type. For example and without limitation, such values and parameters may correspond to margins of the chart and the size, placement, color, and content of various textual or graphical elements of a chart associated with the test type. The chart template may further specify the total range of displayable values for the chart and a chart subrange corresponding to a portion of the total range. In at least certain implementations, the total range may generally correspond to the visually displayed range of the vertical axis of the chart while the chart subrange corresponds to a portion of the vertical axis.

In response, the user computing device 122 then renders and displays the graphical data to display the chart (operation 610). Subsequent to rendering and displaying the chart, the user computing device 122 may receive another selection corresponding to a graphical element of the chart displayed to the user (operation 612). In response, the user computing device 122 may generate and transmit an element selection message to the dosage and topography management system 102 (operation 614) requesting additional data and/or educational content. As discussed above and by way of non-limiting example only, the additional data may include more detailed usage and/or dosage data, educational content relevant to cessation efforts, etc. Accordingly, in response to transmitting the element selection message, the user computing device 122 receives and displays the additional data or curated content (operation 616).

Figure 7:
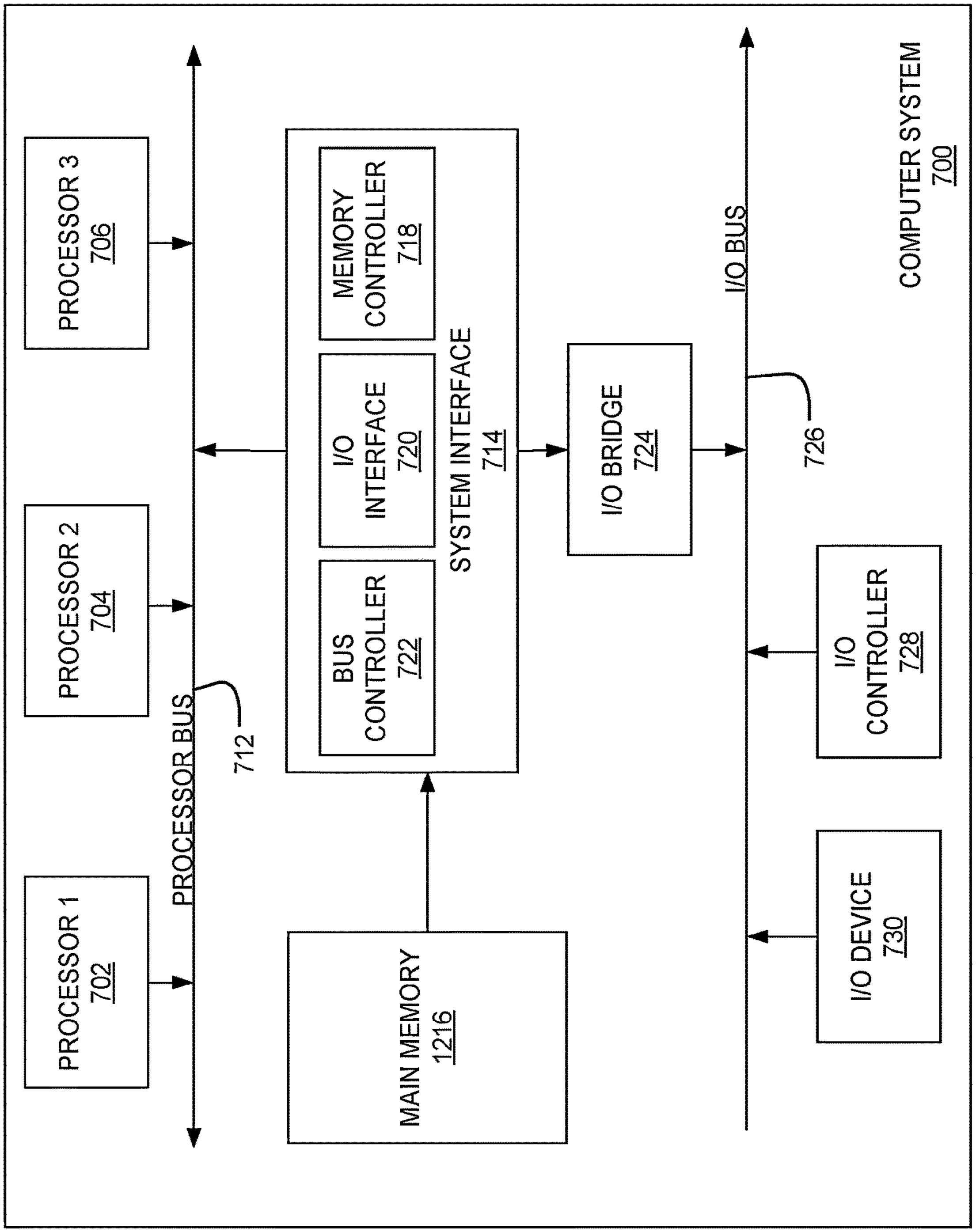
FIG. 7 is a diagram illustrating an example of a computing system which may be used in implementing embodiments of the present disclosure.

FIG. 7 is a block diagram illustrating an example of a user computing device or computer system 700 which may be used in implementing the embodiments of the components of the system disclosed above. The user computing device or computer system (system) includes one or more processors 702-706. Processors 702-706 may include one or more internal levels of cache (not shown) and a bus controller or bus interface unit to direct interaction with the processor bus 712. Processor bus 712, also known as the host bus or the front side bus, may be used to couple the processors 702-706 with the system interface 714. System interface 714 may be connected to the processor bus 712 to interface other components of the system 700 with the processor bus 712. For example, system interface 714 may include a memory controller 718 for interfacing a main memory 716 with the processor bus 712. The main memory 716 typically includes one or more memory cards and a control circuit (not shown). In certain embodiments, aspects of the dosage and topography management system described herein may be stored in the main memory 716 for execution via one or more processors 702-706. System interface 714 may also include an input/output (I/O) interface 720 to interface one or more I/O bridges or I/O devices with the processor bus 712. One or more I/O controllers and/or I/O devices may be connected with the I/O bus 726, such as I/O controller 728 and I/O device 730, as illustrated. The system interface 714 may further include a bus controller 722 to interact with processor bus 712 and/or I/O bus 726.

I/O device 730 may also include an input device (not shown), such as an alphanumeric input device, including alphanumeric and other keys for communicating information and/or command selections to the processors 702-706. Another type of user input device includes cursor control, such as a mouse, a trackball, or cursor direction keys for communicating direction information and command selections to the processors 702-706 and for controlling cursor movement on the display device.

System 700 may include a dynamic storage device, referred to as main memory 716, or a random access memory (RAM) or other computer-readable devices coupled to the processor bus 712 for storing information and instructions to be executed by the processors 702-706. Main memory 716 also may be used for storing temporary variables or other intermediate information during execution of instructions by the processors 702-706. System 700 may include a read only memory (ROM) and/or other static storage device coupled to the processor bus 712 for storing static information and instructions for the processors 702-706. The system set forth in FIG. 7 is but one possible example of a computer system that may employ or be configured in accordance with aspects of the present disclosure.

According to one embodiment, the above techniques may be performed by computer system 700 in response to processor 704 executing one or more sequences of one or more instructions contained in main memory 716 (e.g., instructions related to the dosage and topography management system). These instructions may be read into main memory 716 from another machine-readable medium, such as a storage device. Execution of the sequences of instructions contained in main memory 716 may cause processors 702-706 to perform the process steps described herein. In alternative embodiments, circuitry may be used in place of or in combination with the software instructions. Thus, embodiments of the present disclosure may include both hardware and software components.

A machine readable medium includes any mechanism for storing or transmitting information in a form (e.g., software, processing application) readable by a machine (e.g., a computer). Such media may take the form of, but is not limited to, non-volatile media and volatile media. Non-volatile media includes optical or magnetic disks. Volatile media includes dynamic memory, such as main memory 716. Common forms of machine-readable medium may include, but is not limited to, magnetic storage medium; optical storage medium (e.g., CD-ROM); magneto-optical storage medium; read only memory (ROM); random access memory (RAM); erasable programmable memory (e.g., EPROM and EEPROM); flash memory; or other types of medium suitable for storing electronic instructions.

The methods, devices and systems of the disclosure may be used with any suitable inhalation delivery device, such as those disclosed in WO 2017/192767 A1 and WO 2019/071008 A1, both of which are herein incorporated by reference in their entireties. By way of non-limiting example, the present methods, devices and systems may be used in connection with the following inhalation delivery device. However, the disclosure is not so limited, and any suitable inhalation delivery device may be used in combination with various aspects of the present systems and methods. In one embodiment, an inhalation delivery device of the disclosure generally includes a housing, a mouthpiece, at least one fluid reservoir disposed in, connected to, or in fluid communication with the housing and the mouthpiece, and at least one ejector mechanism in fluid communication with the reservoir(s). The device may also include at least one differential pressure sensor positioned within the housing configured to electronically breath activate the ejector mechanism(s) upon sensing a pre-determined pressure change within the housing. The device may further include one or more air inlet flow elements to facilitate non-turbulent flow through at least a portion of the interior of the housing. The ejector mechanisms may be configured to generate a controllable plume of an ejected stream of droplets. The ejected stream of droplets may be generated from compositions including, without limitation, solutions, suspensions or emulsions which have viscosities and surface tensions in a range capable of droplet formation using the ejector mechanism. Each ejector mechanism may include a piezoelectric actuator, which is directly or indirectly coupled to an aperture plate having a plurality of openings formed through its thickness. The piezoelectric actuator is operable to directly or indirectly oscillate the aperture plate at a frequency to thereby generate an ejected stream of droplets. In certain embodiments, the aperture plate may have a hydrophilic coating on at least the fluid intake surface thereof, and an optional hydrophobic coating on the fluid exit surface thereof.

As shown in further detail herein, the droplet delivery device is configured in an orientation in that the housing, its internal components, and various device components (e.g., the mouthpiece, air inlet flow element, etc.) are orientated in a substantially in-line or parallel configuration (e.g., along the airflow path) so as to form a small, hand-held device.

In certain embodiments, the housing and ejector mechanism are oriented such that the exit side of aperture plate is perpendicular to the direction of airflow and the stream of droplets is ejected in parallel to the direction of airflow. In other embodiments, the housing and ejector mechanism are oriented such that the exit side of aperture plate is parallel to the direction of airflow and the stream of droplets is ejected substantially perpendicularly to the direction of airflow such that the ejected stream of droplets is directed through the housing at an approximate 90 degree change of trajectory prior to expulsion from the housing.

In specific embodiments, the ejector mechanism is electronically breath activated by at least one differential pressure sensor located within the housing and/or mouthpiece of the inhalation delivery device upon sensing a pre-determined pressure change within the mouthpiece and/or housing. In certain embodiments, such a pre-determined pressure change may be sensed during an inspiration cycle by a user of the device.

The ejector mechanism may be comprised of an aperture plate that is directly or indirectly coupled to a piezoelectric actuator. In certain implementations, the aperture plate may be coupled to an actuator plate that is coupled to the piezoelectric actuator. The aperture plate generally includes a plurality of openings formed through its thickness and the piezoelectric actuator directly or indirectly (e.g. via an actuator plate) oscillates the aperture plate, having fluid in contact with one surface of the aperture plate, at a frequency and voltage to generate a directed aerosol stream of droplets through the openings of the aperture plate into the lungs, as the patient inhales. In other implementations where the aperture plate is coupled to the actuator plate, the actuator plate is oscillated by the piezoelectric oscillator at a frequency and voltage to generate a directed aerosol stream or plume of aerosol droplets.

Several features of the device allow precise dosing of specific droplet sizes. Droplet size is set, in part, by the diameter of the openings of the aperture plate, which may be formed with high accuracy. By way of example, the openings in the aperture plate may range in size from about 0.7 μm to about 200 μm, about 0.7 μm to about 100 μm, about 0.7 μm to about 60 μm, about 0.7 μm to about 40 μm, about 0.7 μm to about 20 μm, about 0.7 μm to about 5 μm, about 0.7 μm to about 4.7 μm, about 0.7 μm to about 4 μm, about 0.7 μm to about 3.0 μm, about 0.7 μm to about 2.5 μm, about 0.7 μm and about 2.0 μm, about 0.7 μm and about 1.5 μm, about 0.7 μm and about 1.0 μm, about 5 μm to about 20 μm, about 5 μm to about 10 μm, and combinations thereof. A single aperture plate may include openings having diameters of the same average diameter (within manufacturing tolerances), or a single aperture plate may have openings having diameters of different average diameter. By way of non-limiting example, the same aperture plate may have openings having an average diameter between about 0.7 μm to about 5 μm, and openings having an average diameter between about 5 μm to about 20 μm. The same device may also may multiple ejector mechanisms, and therefore multiple aperture plates, each having their own distance opening size distribution. However, other combinations of opening sizes are envisioned as within the scope of the present disclosure.

In other aspects, ejection rate, in droplets per second, is generally fixed by the frequency of the aperture plate vibration, e.g., 108-kHz, which is actuated by a device microprocessor upon activation of the ejection cycle (e.g., upon detection of inhalation by one or more pressure sensors of the device). In certain embodiments, there is less than a 50-millisecond lag between the detection of the start of inhalation and full droplet generation.

In some aspects, the inhalation delivery device further includes one or more air inlet flow elements positioned in the airflow of the housing and configured to facilitate non-turbulent (i.e., laminar and/or transitional) airflow through at least a portion of the interior of the housing, e.g., across the exit side of aperture plate, and to provide sufficient airflow to ensure that the ejected stream of droplets flows through the droplet delivery device during use. In some embodiments, the air inlet flow element(s) may be positioned within the mouthpiece and/or at an airflow entrance of the housing. In certain embodiments, one or more air inlet flow element(s) may be positioned behind the exit side of the aperture plate along the direction of airflow, in-line or in front of the exit side of the aperture plate along the direction of airflow, and/or in the mouthpiece. In certain embodiments, the air inlet flow element(s) may comprise one or more openings formed there-through, and configured to increase or decrease internal pressure resistance within the inhalation delivery device during use. For instance, the air inlet flow element(s) may comprise an array of one or more openings. In certain embodiments, the air inlet flow element(s) may comprise one or more baffles, e.g., wherein the one or more baffles comprise one or more airflow openings.

In certain embodiments, the inhalation delivery device is comprised of a separate, combination reservoir and ejector mechanism, wherein the ejector mechanism is interfaced with the fluid reservoir (e.g., reservoir/ejector ampoule), and a handheld base unit (e.g., housing) including a microprocessor and power source (e.g., batteries). In certain embodiments, the microprocessor controls dose delivery, dose counting and software designed to monitoring parameters that can be transmitted through blue-tooth technology.

In certain embodiments, the combination reservoir/ejector mechanism (e.g., reservoir/ejector ampoule) that may be replaceable or disposable either on a periodic basis, e.g., a daily, weekly, monthly, as-needed, etc. basis, as may be suitable for the intended use. The reservoir may be prefilled or filled at use via a suitable injection or fill mechanism. In certain aspects, such disposable/replaceable, combination reservoir/ejector mechanism may minimize and prevent buildup of surface deposits or surface microbial contamination on the aperture plate, owing to its short in-use time.

In certain embodiments, the mouthpiece may be interfaced with (and optionally removable and/or replaceable), integrated into, or part of the housing. In other embodiments, the mouthpiece may be interfaced with (and optionally removable and/or replaceable), integrated into, or part of the reservoir or combination reservoir/ejector mechanism. Further, the breath activation pressure sensor(s) may be located in the mouthpiece and/or the housing.

In certain embodiments, the inhalation delivery device is configured so as to be altitude insensitive. For example, the inhalation delivery device is generally insensitive to pressure differentials that may occur when the user travels from sea level to sub-sea levels and at high altitudes, e.g., while traveling in an airplane where pressure differentials may be as great as 4 psi. In certain implementations, the inhalation delivery device may include a superhydrophobic filter, optionally in combination with a spiral vapor barrier, which provides for free exchange of air into and out of the reservoir, while blocking moisture or fluids from passing into the reservoir, thereby reducing or preventing fluid leakage or deposition on aperture plate surfaces.

In certain embodiments, the droplet delivery device may be turned on and activated for use by inserting the reservoir/ejector ampoule into the base unit, opening the mouthpiece cover, and/or switching an on/off switch/slide bar, etc. In certain embodiments, visual and/or audio indicators may be used to indicate the status of the device in this regard, e.g., on, off, stand-by, preparing, etc. By way of example, one or more LED lights may turn green and/or flash green to indicate the device is ready for use. In other embodiments, visual and/or audio indicators may be used to indicate the status of the reservoir/ejector ampoule, including the number of doses taken, the number of doses remaining, instructions for use, etc. For example, and LED visual screen may indicate a dose counter numerical display with the number of remaining doses in the reservoir.

As described in further detail herein, during use as a user inhales through the mouthpiece of the device, a differential pressure sensor within the device may detect inspiratory flow, e.g., by measuring the pressure drop across a Venturi plate at the back of the mouthpiece. When a threshold pressure decline (e.g., 8 SLM) is attained, the microprocessor may activate the ejector mechanism(s), which in turn generate an ejected stream of droplets into the airflow of the device that the user inhales through the mouthpiece. In certain embodiments, audio and/or visual indicates may be used to indicate that dosing has been initiated, e.g., one or more LEDs may illuminate green. The microprocessor then deactivates the ejector at a designated time after initiation so as to achieve a desired administration dosage, e.g., 1-1.45 seconds. Alternatively, the microprocessor may activate the ejector mechanism(s) until such time as the threshold pressure change is no longer detected within the device (indicating that the user is no longer applying inspiratory flow through the device). In certain embodiments, the device may provide visual and/or audio indicators to indicate dosing.

Following dosing, the droplet delivery device may turned off and deactivated in any suitable manner, e.g., by closing a mouthpiece cover, switching an on/off switch/slide bar, timing out from non-use, removing the reservoir/ejector ampoule, etc. If desired, audio and/or visual indicators may prompt a user to deactivate the device, e.g., by flashing one or more red LED lights, providing voice commands to close the mouthpiece cover, etc.

In certain embodiments, the inhalation delivery device may include an ejector mechanism closure system that seals the aperture plate when not in use to protect the integrity of the aperture plate and to minimize and prevent contamination and evaporation of the fluid within the reservoir. For example, in some embodiments, the device may include a mouthpiece cover that comprises a rubber plug that is sized and shaped to seal the exit side surface of the aperture plate when the cover is closed. In other embodiments, the mouthpiece cover may trigger a slide to seal the exit side surface of the aperture plate when the cover is closed. Other embodiments and configurations are also envisioned, e.g., manual slides, covers, and plugs, etc. In certain aspects, the microprocessor may be configured to detect when the ejector mechanism closure, aperture plate seal, etc. is in place, and may thereafter deactivate the device.

Other aspects of the device of the disclosure that allow for precise dosing of specific droplet sizes include the production of droplets within the respirable range early in the inhalation cycle, thereby minimizing the amount of composition being deposited in the mouth or upper airways at the end of an inhalation. In addition, the design of the fluid ampoule allows the aperture plate surface to be wetted and ready for ejection without user intervention, thus obviating the need for shaking and priming. Further, the design of the fluid ampoule vent configuration together with the ejector mechanism closure system limits fluid evaporation from the reservoir to less than 150 μL to 350 μL per month.

The device may be constructed with materials currently used in FDA cleared devices. Standard manufacturing methods may be employed to minimize extractables.

Any suitable material may be used to form the housing of the droplet delivery device. In particular embodiment, the material should be selected such that it does not interact with the components of the device or the fluid to be ejected (e.g., nicotine, THC, active agent, etc.). For example, polymeric materials suitable for use in pharmaceutical applications may be used including, e.g., gamma radiation compatible polymer materials such as polystyrene, polysulfone, polyurethane, phenolics, polycarbonate, polyimides, aromatic polyesters (PET, PETG), etc.

The reservoir/ejector ampoule may be constructed of any suitable materials for the intended composition use. In particular, the fluid contacting portions may be made from material compatible with the desired agent(s), e.g., nicotine, THC, active agent, etc. By way of example, in certain embodiments, the composition only contacts the inner side of the fluid reservoir and the inner face of the aperture plate and piezoelectric element. Wires connecting the piezoelectric ejector mechanism to the batteries contained in the base unit may be embedded in the ampoule shell to avoid contact with the composition. The piezoelectric ejector may be attached to the fluid reservoir by a flexible bushing. To the extent the bushing may contact the composition, it may be, e.g., any suitable material known in the art for such purposes such as those used in piezoelectric nebulizers.

In certain embodiments, the device mouthpiece may be removable, replaceable and may be cleaned. Similarly, the device housing and ampoule can be cleaned by wiping with a moist cloth. In certain embodiments, the mouthpiece may be interfaced with (and optionally removable and/or replaceable), integrated into, or part of the housing. In other embodiments, the mouthpiece may be interfaced with (and optionally removable and/or replaceable), integrated into, or part of the reservoir/ejector ampoule.

Again, any suitable material may be used to form the mouthpiece of the inhalation delivery device. In particular embodiment, the material should be selected such that it does not negatively interact with the components of the device or the fluid to be ejected (e.g., nicotine, THC, active agent, etc.). For example, polymeric materials suitable for use in pharmaceutical applications may be used including, e.g., gamma radiation compatible polymer materials such as polystyrene, polysulfone, polyurethane, phenolics, polycarbonate, polyimides, aromatic polyesters (PET, PETG), etc. In certain embodiments, the mouthpiece may be removable, replaceable and sterilizable. This feature improves sanitation for droplet delivery by providing a mechanism to minimize buildup of aerosolized compositions within the mouthpiece and by providing for ease of replacement, disinfection and washing. In one embodiment, the mouthpiece tube may be formed from sterilizable and transparent polymer compositions such as polycarbonate, polyethylene or polypropylene, as discussed herein.

In certain aspects of the disclosure, an electrostatic coating may be applied to the one or more portions of the housing, e.g., inner surfaces of the housing along the airflow pathway such as the mouthpiece, to aid in reducing deposition of ejected droplets during use due to electrostatic charge build-up. Alternatively, one or more portions of the housing may be formed from a charge-dissipative polymer. For instance, conductive fillers are commercially available and may be compounded into the more common polymers used in medical applications, for example, PEEK, polycarbonate, polyolefins (polypropylene or polyethylene), or styrenes such as polystyrene or acrylic-butadiene-styrene (ABS) copolymers. Alternatively, in certain embodiments, one or more portions of the housing, e.g., inner surfaces of the housing along the airflow pathway such as the mouthpiece, may be coated with anti-microbial coatings, or may be coated with hydrophobic coatings to aid in reducing deposition of ejected droplets during use. Any suitable coatings known for such purposes may be used, e.g., polytetrafluoroethylene (Teflon).

Any suitable differential pressure sensor with adequate sensitivity to measure pressure changes obtained during standard inhalation cycles may be used, e.g., ±5 SLM, 10 SLM, 20 SLM, etc. For instance, pressure sensors from Sensirion, Inc., SDP31 or SDP32 (U.S. Pat. No. 7,490,511 B2) are particularly well suited for these applications.

Embodiments of the present disclosure include various steps, which are described in this specification. The steps may be performed by hardware components or may be embodied in machine-executable instructions, which may be used to cause a general-purpose or special-purpose processor programmed with the instructions to perform the steps. Alternatively, the steps may be performed by a combination of hardware, software, and/or firmware.

The description above includes example systems, methods, techniques, instruction sequences, and/or computer program products that embody techniques of the present disclosure. However, it is understood that the described disclosure may be practiced without these specific details. In the present disclosure, the methods disclosed may be implemented as sets of instructions or software readable by a device. Further, it is understood that the specific order or hierarchy of steps in the methods disclosed are instances of example approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

While the present disclosure has been described with reference to various embodiments, it should be understood that these embodiments are illustrative and that the scope of the disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

What is claimed:

1. A method for controlling a desired dose of a composition for delivery to a pulmonary system of a user via an inhalation delivery device comprising:

receiving, at a computing system based on user input, a request for a desired dose of at least one agent or ingredient of a composition for delivery to the pulmonary system of the user via inhalation, wherein the computing system includes a predetermined desired inhalation topography for the user defined as a stored functional relationship mapping inhalation flow rate to drug dispense rate;

at the computing system and in response to receiving the request, determining inhalation delivery device operating parameters of the inhalation delivery device to provide the requested desired dose of the at least one agent or ingredient of the composition for delivery to the pulmonary system of a user via inhalation, wherein the inhalation delivery device operating parameters are configured to require that the drug dispense rate corresponds to the inhalation flow rate according to the stored functional relationship;

generating, at the computing system, computer executable instructions for activation and operation of the inhalation delivery device;

transmitting the instructions to an electronically controlled droplet ejector including at least one droplet ejection element;

wherein the instructions include setting a maximum drug dispense rate such that the drug dispense rate increases with the inhalation flow rate up to an optimal inhalation flow rate and thereafter saturates at the maximum drug dispense rate, thereby training the user toward the optimal inhalation flow rate; and wherein the instructions further include micro-stops during a continuous dispense period to modulate dispense rate in accordance with the inhalation flow rate.

2. The method of claim 1, further comprising progressively adjusting dosage windows or the inhalation topography to provide for controlled cessation of use of the at least one agent or ingredient by the user.

3. The method of claim 1, wherein the inhalation topography includes an initial bolus dose at an initial loading dose followed by maintenance doses at reduced dose.

4. The method of claim 1, wherein the request includes independently selected doses of at least two agents or ingredients such that instructions are provided to the inhalation delivery device to independently control dosing of each of said at least two agents or ingredients separately.

5. The method of claim 1, wherein the composition comprises nicotine.

6. The method of claim 4, wherein the at least two agents or ingredients include nicotine and a flavoring.

7. The method of claim 1, wherein the computing system is a mobile computing device of the user, and the user input is received via a user interface of the mobile computing device.

8. The method of claim 1, wherein the inhalation delivery device includes the computing system, and the user input is received from one or both of a user interface of the inhalation delivery device and detecting user inhalation flow rate from the user.

9. The method of claim 8, wherein the user interface of the inhalation delivery device comprises user input buttons, an LCD touchscreen, or combinations thereof.

10. A computing system comprising:

one or more processors; and a memory storing first instructions executable by the one or more processors, wherein execution causes the one or more processors to:

receive a request for a desired dose of at least one agent or ingredient of a composition for delivery to a pulmonary system of a user via an inhalation delivery device, wherein the computing system includes a predetermined desired inhalation topography defined as a stored functional relationship mapping inhalation flow rate to drug dispense rate;

determine inhalation delivery device operating parameters of the inhalation delivery device configured to require the drug dispense rate correspondence to the inhalation flow rate according to the stored functional relationship;

generate computer executable second instructions for activation and operation of the inhalation delivery device;

transmit the second instructions to an electronically controlled droplet ejector including at least one droplet ejection element;

wherein the second instructions include saturation of the drug dispense rate at an optimal inhalation flow rate and micro-stop modulation during a continuous dispense period.

11. The computing system of claim 10, wherein the first and second instructions further cause the one or more processors to progressively adjust dosage windows or the inhalation topography to provide for controlled cessation of use of the at least one agent or ingredient by the user.

12. The computing system of claim 10, wherein the inhalation topography includes an initial bolus dose at an initial loading dose followed by maintenance doses at reduced dose.

13. The computing system of claim 10, wherein the computing system is a mobile computing device of the user, and the user input is received via a user interface of the mobile computing device.

14. The computing system of claim 10, wherein the inhalation delivery device includes the computing system and the user input is received from one or both of a user interface of the inhalation delivery device and detecting user inhalation flow rate from the user.

15. The computing system of claim 14, wherein the user interface of the inhalation delivery device comprises user input buttons, an LCD touchscreen, or combinations thereof.

* * * * *